(12) United States Patent
Bernard et al.

(10) Patent No.: US 7,521,422 B2
(45) Date of Patent: Apr. 21, 2009

(54) USE OF ASPARTIC PROTEASES IN COSMETICS AND THERAPEUTICS

(75) Inventors: Dominique Bernard, Paris (FR); Bruno Mehul, Gourdon (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/520,521

(22) PCT Filed: Jul. 9, 2003

(86) PCT No.: PCT/FR03/02151

§ 371 (c)(1),
(2), (4) Date: Nov. 15, 2005

(87) PCT Pub. No.: WO2004/007548

PCT Pub. Date: Jan. 22, 2004

(65) Prior Publication Data

US 2006/0240053 A1    Oct. 26, 2006

(30) Foreign Application Priority Data

Jul. 9, 2002 (FR) .................................. 02 08613

(51) Int. Cl.
*C07K 14/00* (2006.01)
*C07K 19/00* (2006.01)
*A61K 38/48* (2006.01)

(52) U.S. Cl. ............................. 514/12; 514/2; 530/350; 530/412; 424/9.1; 424/401; 424/78.02

(58) Field of Classification Search ..................... 514/2, 514/12; 530/350, 412; 424/9.1, 401, 78.02
See application file for complete search history.

(56) References Cited

U.S. PATENT DOCUMENTS

| 5,545,402 | A | 8/1996 | Watkinson |
| 6,274,364 | B1 | 8/2001 | Bernard et al. |
| 6,645,509 | B1 | 11/2003 | Serre et al. |
| 6,737,055 | B2 | 5/2004 | Bernard et al. |
| 6,979,557 | B2 * | 12/2005 | Isogai et al. ............... 435/69.1 |
| 2003/0206896 | A1 | 11/2003 | O'Prey et al. |

FOREIGN PATENT DOCUMENTS

| DE | 19950020 A | 4/2001 |
| FR | 2761363 A | 10/1998 |
| JP | A-11-139933 | 5/1999 |
| WO | WO 01/62788 A2 | 8/2001 |
| WO | 02/22101 A | 3/2002 |

OTHER PUBLICATIONS

Janson et al. "Protein purification: principles, high resolution methods, and applications/", Book xi, 502p, 1989, published by VCH, New York, New York, summary.

Mehul et al., "Identification and Cloning of a New Calmodulin-like Protein from Human Epidermis", The Journal of Biological Chemistry, vol. 275, No. 17, pp. 12841-12847, 2000, published by the American Society for Biochemistry and Molecular Biology, Inc., US.

Meek et al., "Human immunodeficiency virus 1 protease expressed in *Escherichia coli* behaves as a dimeric aspartic protease", Proc. Natl. Acad. Sci, vol. 86, pp. 1841-1845, Mar. 1989, Biochemistry, published by the National Academy of Sciences for the United States, US.

Kyte et al., "A Simple Method for Displaying the Hydropathic Character of a Protein", J. Mol. Biol., vol. 157, pp. 105-132, 1982, published by Academic Press Inc. (London) Ltd., London, GB.

Sugano et al., "*Homo sapiens* CDNA FLJ25084 FIS, Clone CBL 08511", EMBL., AK 057813, Oct. 31, 2001.

Isogai et al., "*Homo sapiens* CDNA FLJ31432 FIS, Clone NT2NE 2000550", EMBL., AK 055994, Oct. 31, 2001 and Aug. 6, 2002.

"1998 Biochemicals Catalog, Proteases for Cleavage and Sequencing", Boehringer Mannheim Biochemicals Catalog, XX, XX, 1998, pp. 404-410.

Rawlings et al. Methods in Enzymology, Academic Press, Inc., San Diego, CA, vol. 248, 1995, pp. 105-120.

Russell, "Topical Therapy for Acne", http://www aafp org/afp/20000115/357 html, American Family Physician, vol. 61/No. 2, 357-366 (downloaded as pp. 1-9), 2000, American Academy of Family Physicians, United States.

Ahnini et al, "Novel genetic association between the corneodesmosin (MHC S) gene and susceptibility to psoriasis", Human Molecular Genetics, vol. 8, No. 6, pp. 1135-1140, Oxford University Press, England, (1999).

Lundström et al, "Evidence for a role of corneodesmosin, a protein which may serve to modify desmosomes during cornification, in a stratum corneum cell cohesion and desquamation", Arch Dermatol Res, vol. 286, pp. 369-375, 1994, Springer-Verlag, Germany.

Burdette-Taylor SR, "Eczema, ichthyosis, psoriasis: conditions of *cornification*", Ostomy Wound Manage, vol. 41, No. 7, pp. 36-8, 40, 42, 1995. Health Management Publications, United States.

Resnick B, "Dermatologic problems in the elderly", Lippincotts Prim Care Pract, vol. 1, No. 1, pp. 14-30; quiz 31-2, 1997, Lippincott Williams & Wilkins, United States.

Strausberg, R. "Accession: AAH31997 [GI:21594225], Definition: Similar to RIKEN cDNA 23000031P22 gene", NCBI Sequence Revision History, Jun. 26, 2002, NCBI URL:http://www.ncbi.nlm.nih.gov/entrez/viewer.fcgi?21594225:OLD12:2619652, retrieved on Apr. 30, 2008 retrieved from the Internet: URL:http://www.ncbi.nlm.nih.gov/entrez/sutils/girevhist.cgi?val=AAH31997.

* cited by examiner

*Primary Examiner*—Chih-Min Kam
(74) *Attorney, Agent, or Firm*—Buchanan, Ingersoll & Rooney P.C.

(57) ABSTRACT

The invention provides a cosmetic or pharmaceutical composition comprising, in a physiologically acceptable medium, at least one purified natural or synthetic polypeptide wherein the peptide sequence is represented wholly or partly by at least one sequence selected from the group consisting of SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 16, SEQ ID NO: 25 and SEQ ID NO: 27 and their homologs.

17 Claims, 5 Drawing Sheets

```
CLUSTAL W (1.81) multiple sequence alignment

FIAV            IGFVNYNKVGTTTTLEKRPEILIFVNGYPIKFLLDTGADITILNRRDFQVKN-----SIE 55
HIV2            ----------PQFSLWKRPVVTAYIEGQPVEVLLDTGADDSIVAG--IELGN-----NYS 43
SASPase         -----------ANSMGKGYYLKGKIGKVPVRFLVDSGAQVSVVHPNLWEEVTDGDLDTLQ 49
                             :: *   :   :   *:..*:*:**: :::     :  .     . .

FIAV            NGRQNMIG-VGGGKRGTNYINVHLEIRDENYKTQCIFGNVCVLEDNSLIQPLLGRDNMIK 114
HIV2            ---PKIVGGIGGFINTKEYKNVEIEVLNKKVRATIMTG-------DTPIN-IFGRNILTA 92
SASPase         PFENVVKVANGAEMKILGVWDTAVSLGKLKLKAQFLVAN------ASAEEAIIGTDVLQD 103
                     :    *.  .     :. :.: . : ::  : .        :  :  ::* : :

FIAV            FNIRLVMAQ-------------------------- 123
HIV2            LGMSLNL---------------------------- 99
SASPase         HNAILDFEHRTCTLKGKKFRLLPVGGSLEDEFDLE 138
                 .  * :

Figure 1:
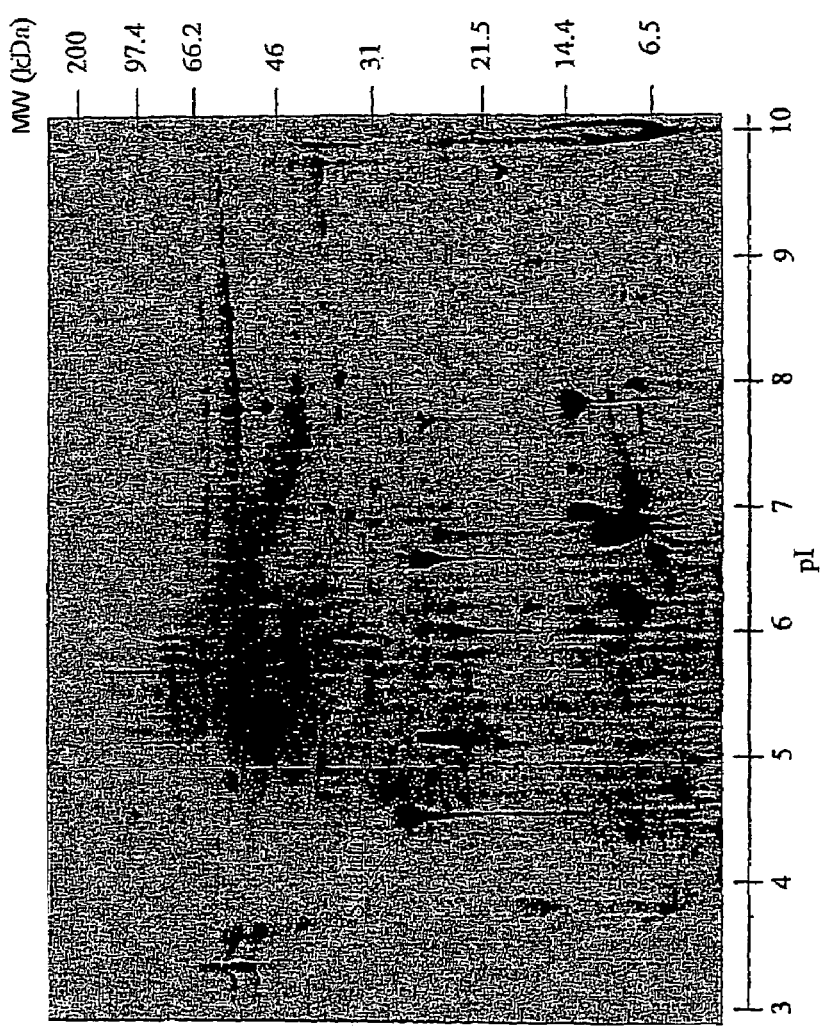

```

USE OF ASPARTIC PROTEASES IN COSMETICS AND THERAPEUTICS

CROSS-REFERENCE TO RELATED APPLICATIONS

This application is the US. national stage of International Application No. PCT/FR03/002151, filed Jul. 9, 2003, and claims priority under 35 U.S.C. §119 of French Patent Application No. 02/08613, filed Jul. 9, 2002, said applications being incorporated by reference herein in their entireties and relied upon.

The present invention relates mainly to the use, in cosmetics and therapeutics, of a novel aspartic acid protease, referred to as SASPase, of the truncated or derived forms of said protein or of a mixture of polypeptides derived from the proteolysis thereof, in particular for the purpose of treating conditions related to a dysfunction of cell proliferation and/or differentiation.

The invention also relates to deoxyribonucleic acid sequences encoding said aspartic acid protease SASPase and its "activated" forms, to the corresponding polypeptide sequences and to the uses of said deoxyribonucleic acid sequences.

Proteases are hydrolytic enzymes capable of cleaving peptide bonds. A certain number of them are, today, known to play an essential role in the equilibrium of the physiology of the epidermis.

The epidermis is conventionally divided into a basal layer of keratinocytes constituting the germinative layer of the epidermis, a "spiny" layer consisting of several layers of polyhedral cells arranged on the germinative layers, one to three "granular" layers consisting of flattened cells containing distinct cytoplasmic inclusions, the keratohyalin granules, and finally, a set of upper layers, called cornified layers (or stratum corneum), consisting of keratinocytes at the terminal stage of their differentiation, called corneocytes.

Corneocytes are anucleated cells consisting mainly of a fibrous material containing cytokeratins, surrounded by a cornified envelope. There is a permanent production of new keratinocytes in order to compensate for the continuous loss of epidermal cells in the cornified layer according to a mechanism called desquamation. An imbalance between the production of cells in the basal layer and the rate of desquamation can in particular result in the formation of scales at the surface of the skin.

As it happens, many skin pathologies are characterized by the production of a thick cornified layer and by abnormal desquamation, i.e. hyperkeratosis. By way of example, mention may be made of:

xerosis (or dryness of the skin),
ichthyoses,
psoriasis,
certain benign or malignant tumor lesions, and
reactive hyperkeratoses.

Conversely, certain pathological manifestations result in a thinning of the epidermis, and more particularly of the cornified layer. This type of manifestation then results in excessive fragility of the cutaneous covering. By way of representation of these conditions, mention may in particular be made of reactions of immune origin, generally induced by being in the presence of or coming into contact with one or more exogenous agents.

Consequently, knowledge of the polypeptides involved in intercorneocyte cohesion is one of the pathways which may make it possible to develop products intended to combat the effects of an excess of or a deficiency in one or more polypeptide(s) of this type, in particular at the surface of the skin.

One of the objects of the invention is precisely to propose the use, for cosmetic and/or therapeutic purposes, of a polypeptide involved in regulating the phenomenon of epidermal differentiation/proliferation.

More precisely, the inventors have demonstrated in human keratinocytes, isolated and purified a polypeptide having, in its peptide sequence (SEQ ID NO 5), the sequence FLVDS-GAQVSVV (SEQ ID NO: 1) corresponding to a PROSITE signature PS00141 of active sites of proteases of the "aspartic acid" protease family.

This polypeptide, also referred to hereinafter as SASPase protein, is, moreover, characterized by the presence, in its peptide sequence, of the following sequences:

```
AQFLVANASAEEAIIGTDVLQ      (SEQ ID NO: 2)

and

ILGVWDTAV                  (SEQ ID NO: 3).
```

Unexpectedly, the inventors have demonstrated that the protein represented by the sequence SEQ ID NO: 5, also referred to as SASPase protein, have significant proteolytic activity, and have in particular noted this activity with respect to casein and to insulin, as shown in the examples hereinafter.

They have, moreover, observed that this SASPase protein is autocatalytic and generates, at a pH of between 3 and 7, and preferably greater than or equal to 4.5, a truncated form referred to as "activated SASPase", corresponding to the sequence SEQ ID NO: 6 capable, in turn, of dimerizing.

One aspect of the invention therefore relates to an isolated and purified polypeptide belonging to the aspartic acid protease family, characterized in that it has a peptide sequence represented by the sequence SEQ ID NO: 6, SEQ ID NO: 16, SEQ ID NO: 25 or SEQ ID NO: 27.

SEQ ID NO: 6 corresponds to an activated form of SEQ ID NO: 5.

SEQ ID NO: 16 corresponds to the sequence SEQ ID NO: 6 which has had its first two amino acids deleted.

The sequence SEQ ID NO: 25 is another activated form of SEQ ID NO: 5. It is obtained from a truncated form of SASPase (SEQ ID NO: 36) from which the site encoding the sequence FANS (SEQ ID NO: 29) has been deleted. It is more particularly generated at pH 5.00 in acetate buffer.

The sequence SEQ ID NO: 27 corresponds to the sequence SEQ ID NO: 25 from which a part of its C-terminal fragment has been deleted.

In general, the invention extends to all the homologous forms of the various polypeptides or peptide sequences mentioned. Conventionally, the expression "homolog of a polypeptide or of a peptide sequence" is intended to mean any polypeptide or any peptide sequence having at least 85%, especially at least 90%, and in particular at least 95% sequence homology, and having, where appropriate, the same type of biological activity as said polypeptide or said peptide sequence.

These homologous forms encompass the variants defined hereinafter.

The invention extends in particular to the homologous forms of the abovementioned polypeptides, i.e. the forms showing the same biological activity and having at least 85%, especially at least 90%, and in particular at least 95% sequence homology with the sequence SEQ ID NO: 6, SEQ ID NO: 16, SEQ ID NO: 25 or SEQ ID NO: 27.

Similarly, the invention extends to the proteins having at least 30% homology with the sequence SEQ ID NO: 6, SEQ ID NO: 16 or SEQ ID NO: 25, on the condition that the homology with the sequence of the active site SEQ ID NO: 1 contained in SEQ ID NO: 6, SEQ ID NO: 16, SEQ ID NO: 25 and SEQ ID NO: 27 is at least 80%.

The invention also extends to the proteins having both the "aspartyl protease retroviral type" unit defined under the PROSITE unit reference: PS50175, and also at least one transmembrane domain as predicted by the algorithms recognized for such a detection, among which mention may be made of: PRED-TMR2, TMHMM, TMpred and SOSUI.

The modifications, also referred to as mutations or variations, according to the invention can derive either from the deletion of one or more amino acids of the sequence SEQ ID NO: 6, SEQ ID NO: 16, SEQ ID NO: 25 or SEQ ID NO: 27, or from the addition of one or more amino acids to the sequence SEQ ID NO: 6, SEQ ID NO: 16, SEQ ID NO: 25 or SEQ ID NO: 27, or alternatively from the substitution of one or more amino acids for the sequence SEQ ID NO: 6, SEQ ID NO: 16, SEQ ID NO: 25 or SEQ ID NO: 27. The corresponding sequences are also referred to under the term "variants" in the context of the present invention.

By way of illustration of the deletion variants, mention may more particularly be made of the following peptide sequences:

the sequence SEQ ID NO: 4 corresponding to SEQ ID NO: 5 truncated in terms of its N-terminal fragment Δ1-84;

the sequence SEQ ID NO: 7 corresponding to the sequence of the N-terminal portion of the SASPase protein (SEQ ID NO: 5). The interaction of this fragment with a biological ligand could be an important step for the activation of the SASPase protein, and in particular the generation of its activated form (SEQ ID NO: 6);

the sequence SEQ ID NO: 8 corresponding to the sequence of the "transmembrane" portion of the SASPase protein (SEQ ID NO: 5);

the sequence SEQ ID NO: 9 corresponding to the sequence of a peptide derived from the C-terminal portion of the SASPase protein (SEQ ID NO: 5);

the sequences SEQ ID NO: 29 and SEQ ID NO: 30 corresponding to two activation sites.

Also covered under the term "variant" are the proteins from fusion of the SASPase protein (SEQ ID NO: 5), or of its activated forms SEQ ID NO: 6, SEQ ID NO: 16, SEQ ID NO: 25 or SEQ ID NO: 27, with another polypeptide, a hydrophilic or hydrophobic targeting agent or a bioconversion precursor capable in particular of controlling the activation of said protein.

It is known that polypeptides can undergo post-translational modifications such as the formation of disulfide bonds, specific proteolytic cleavages, the addition of carbohydrates (glycosylation), phosphorylation, in particular on serines and/or threonines and/or tyrosines, and/or association with lipids.

The polypeptide of the invention may have undergone one or more post-translational modifications. In particular, the polypeptides according to the invention can be N-glycosylated, phosphorylated, myristoylated, amidated and/or citrilinated.

Thus, the invention also relates to the claimed polypeptides which may or may not have undergone post-translational modifications.

The invention also extends to the multimeric forms, and preferably to the dimeric form of the peptide sequence SEQ ID NO: 6, SEQ ID NO: 16, SEQ ID NO: 25 or SEQ ID NO: 27. The dimeric form of the peptide sequence SEQ ID NO: 6 is in particular characterized in example V hereinafter. It can in particular be obtained by molecular association of the monomeric form or by expression of its cDNA encoding the active dimer, incorporating, by way of bonding agent between the two monomeric entities, a unit made up of 2 to 6 amino acids.

The claimed polypeptides may be of natural or synthetic origin. The term "synthetic" is here intended to mean any polypeptide obtained chemically or by production in an organism after introduction into this organism of the elements required for this production.

They may be derived from any possible origin, namely either animal, in particular mammalian or even more particularly human origin, or plant origin, or from microorganisms (for example viruses, phages, bacteria, yeast, inter alia) or else from fungi, or derived from overexpression in a eukaryotic system, for example a mammalian cell, without any prejudice as to whether or not they are naturally present in said organism of origin.

In particular, the polypeptides in accordance with the invention are of natural origin, purified from mammalian tissues, more particularly from mammalian skin.

In particular, they are purified from human skin, and even more particularly from human epidermis.

It is known that, in a polypeptide, one or more amino acid residues can be replaced with amino acid residues having a similar hydropathic index without, however, changing the biological properties of the polypeptide.

The hydropathic index is an index assigned to amino acids as a function of their hydrophobicity and of their charge (Kyte et al. (1982), J. Mol. Biol., 157: 105).

Thus, a subject of the invention is also a polypeptide as described above, in which at least one amino acid residue has been replaced with an amino acid residue having a similar hydropathic index.

The polypeptides can also be classified according to their isoelectric point.

The theoretical isoelectric point of a polypeptide can be deduced from its amino acid chain. The polypeptides of the invention are theoretically acid polypeptides.

Thus, the polypeptides of sequence SEQ ID NO: 5, SEQ ID NO: 6 or SEQ ID NO: 16 have an isoelectric point of between 3 and 9, more particularly of between 4 and 6, and especially of approximately 5.8.

It is also known that the primary amino acid sequence and also the various post-translational modifications that a polypeptide undergoes mean that said polypeptide can be characterized by its apparent molecular mass expressed in kilodaltons.

The term "apparent molecular mass" is intended to mean the molecular mass obtained for the polypeptide by comparison of the electrophoretic mobility thereof with those of standard proteins of known molecular weights on polyacrylamide/sodium dodecyl sulfate gel, or else by comparison of the polypeptide elution volume with that of standard proteins of known molecular weights in exclusion chromatography (according to the techniques described in "Protein Purification", J.-C. Janson and L. Ryden, VCH Publisher Inc. N.Y., 1989). (The method selected in the context of the invention is that based on electrophoretic mobility).

Knowledge of the amino acid chain of the polypeptide of the invention makes it possible to determine the theoretical molecular weight thereof.

The invention therefore relates to a polypeptide of sequence SEQ ID NO: 6 having an apparent molecular mass of between 5 and 30 kilodaltons (kD), especially of between 9 and 15 kD, and more particularly of between 11 and 14 kD. In particular, this polypeptide of the invention has an apparent molecular mass of the order of 12 kD.

As emerges from the examples presented hereinafter, the inventors have characterized the expression of the polypeptide for which the sequence is represented by the sequence SEQ ID NO: 5, in a large number of human biological tissues such as fetal liver, placenta, muscle, lung or small intestine, and especially in the brain and the heart, and more particularly in the epidermis where the expression is particularly high.

It has, moreover, been noted that the SASPase of sequence SEQ ID NO: 5 degrades corneodesmosin, which is a marker of desquamation.

Finally, the presence, in the polypeptide sequence, of the SASPase (SEQ ID NO: 5), of an autocatalytic site corresponding to a site described for protease of the matrilysin type capable of activating type 1, 2 and 9 MMPs, reflects a potential activity of the SASPase, and also of its activated forms (SEQ ID NO: 6, SEQ ID NO: 16, SEQ ID NO: 25 or SEQ ID NO 27) or of its fragments, on endogenous substrates, and therefore of potential applications in cicatrization, re-epithialization, aging, angiogenesis and cancerization (invasion process) for said protein and its various activated forms or fragments.

All this information therefore validates the involvement of the polypeptide in accordance with the invention in the process of cell proliferation and/or differentiation and identifies it as a novel dermato/cosmetological and therapeutic target.

Consequently, a second aspect of the invention relates to a cosmetic or pharmaceutical composition comprising, in a physiologically acceptable medium, at least one purified, natural or synthetic polypeptide, the sequence of which comprises at least one peptide sequence represented wholly or partly by at least one sequence chosen from SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 16, SEQ ID NO: 25 and SEQ ID NO: 27 and homologs thereof.

In particular, the present invention relates to a cosmetic or pharmaceutical composition comprising, in a physiologically acceptable medium, at least one purified, natural or synthetic polypeptide, the peptide sequence of which is represented wholly or partly by the sequence SEQ ID NO: 5, SEQ ID NO: 6, SEQ ID NO: 7, SEQ ID NO: 16 or SEQ ID NO: 25 or SEQ ID NO: 27, or homologs thereof, and in particular which is represented by the peptide sequence SEQ ID NO: 5, SEQ ID NO: 6, SEQ ID NO: 7, SEQ ID NO: 16, SEQ ID NO: 25 or SEQ ID NO: 27.

The present invention also relates to a cosmetic or pharmaceutical composition comprising at least one purified, natural or synthetic polypeptide, the peptide sequence of which is represented wholly or partly by at least one sequence chosen from SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 16, SEQ ID NO: 25 and SEQ ID NO: 27, and homologs thereof, and in particular at least one polypeptide of sequence SEQ ID NO: 5, SEQ ID NO: 6, SEQ ID NO: 7, SEQ ID NO: 16, SEQ ID NO: 25 or SEQ ID NO: 27, in a multimeric, and preferably dimeric, form.

For the purpose of the invention, and unless otherwise indicated, the term "polypeptide" is intended to cover, in the claimed compositions, natural or synthetic polypeptides, whether they are obtained by proteolysis or by synthesis, the various post-translational forms thereof and in particular those described above, or else any natural or synthetic polypeptide, the sequence of which consists wholly or partly of the abovementioned sequences, such as, for example, the variants described above.

The present invention also relates to a cosmetic or pharmaceutical composition in which said polypeptide is in the form of a polypeptide of sequence SEQ ID NO: 5, SEQ ID NO: 6, SEQ ID NO: 7, SEQ ID NO: 16, SEQ ID NO: 25 or SEQ ID NO: 27, fused with another polypeptide, a hydrophilic or hydrophobic targeting agent or a bioconversion precursor.

It is, moreover, known that the primary amino acid sequence of a polypeptide determines sites specifically recognized by proteases which, once the recognition of these sites is effective, will, with or without binding to said polypeptide, induce cleavage thereof by proteolysis.

Consequently, the invention is also directed toward a cosmetic or pharmaceutical composition comprising, in a physiologically acceptable medium, at least one polypeptide mixture derived from the proteolysis of a polypeptide, the sequence of which is represented wholly or partly by the sequence SEQ ID NO: 5, SEQ ID NO: 6, SEQ ID NO: 7, SEQ ID NO: 16, SEQ ID NO: 25 or SEQ ID NO: 27, or homologs thereof, and more particularly the sequence of which is represented by SEQ ID NO: 5, SEQ ID NO: 6, SEQ ID NO: 7, SEQ ID NO: 16, SEQ ID NO: 25 or SEQ ID NO: 27.

The amount of polypeptide contained in the compositions of the invention depends, of course, on the desired effect and can therefore vary to a large extent.

To give an order of magnitude, the composition can contain a polypeptide in accordance with the invention in an amount representing from 0.00001% to 50% of the total weight of the composition, and preferably in an amount representing from 0.001% to 10% of the total weight of the composition, and even more preferably in an amount representing from 0.1% to 1% of the total weight of the composition.

As described above, a certain number of disorders are associated with cell differentiation and/or proliferation conditions. Insofar as the polypeptides in accordance with the invention are involved in the regulation of these two phenomena, they advantageously constitute potential targets for treating any disorder resulting from a dysfunction of cell proliferation or differentiation, in particular epidermal cell proliferation or differentiation. Consequently, besides the fact that the polypeptides according to the invention can be used directly as active material in a cosmetic or pharmaceutical composition, they can also themselves serve as a target in a cosmetic or pharmaceutical treatment or be used as diagnostic tools.

The inventors have, moreover, characterized the presence of cleavage sites in the peptide sequence SEQ ID NO: 5, partly located in its N-terminal portion and also present in the active forms SEQ ID NO: 6 and SEQ ID NO: 16 and partly present in its C-terminal portion and also present in the active forms SEQ ID NO: 25 and SEQ ID NO: 27. More precisely, the deduced cleavage sites for the autoactivation of the SASPase itself are F/A, N/S, E/L, A/L, R/F, H/S, F/E, E/A. Evidently, these cleavage sites may be determinant in the activation of the protein, or for blocking it, or conversely for activating its hydrolysis.

The relevant sites more precisely located in the N-terminal region are F/A and N/S, and appear in the FANS sequence referred to as SEQ ID NO: 29. They appear in particular to be involved in generating the activated form represented by SEQ ID NO: 25.

As regards the second potential region for activation or inactivation of the SASPase protein SEQ ID NO: 5, it corresponds more particularly to the sequence DLELIE, referred to as SEQ ID NO: 30, and comprises in particular the cleavage site E/L.

Based on these cleavage sites, it is possible to envision synthesizing various types of peptides that are either modified or carry a quenched fluorophor, and which will serve as a substrate or as inhibitors.

The minimum sequence that can be used is obviously the dipeptide (amino acids on either side of the cleavage site); however, in general, peptides of 8 to 12 amino acids where the cleavage site is in the central position are used. For example, it is known that the SASPase cleaves insulin at the E/A position. It is therefore possible to imagine developing a peptide-type substrate that incorporates this cleavage site, modifying it chemically at each of its ends with a quenched fluorophor group of the type: Abz(NO$_2$)Tyr (N-end: aminobenzoic acid: C-end: nitrotyrosine (amide)). Hydrolysis of this peptide with the protease will separate the fluorophor and the quencher and will therefore be followed by an increase in fluorescence.

Another chemical couple such as Dabcyl/EDANS can be used to create another type of quenched substrate.

It is also possible to envision a chromogenic substrate by coupling the peptide with the para-nitroanilide group.

In the same way, it is possible to envision developing an SASPase-specific inhibitor by replacing one of the amino acids of such a peptide, by modifying the peptide bond or by adding a chemical group so that the bond is made non-hydrolyzable by the enzyme but the peptide still has affinity for the active site. For example, a non-natural amino acid is added, the peptide bond is reduced, or chemical groups of the aldehyde, chloromethyl ketone or diazomethyl ketone type are added.

The inventors have in particular shown that point modifications introduced into the peptide substrate represented by SEQ ID NO: 30 may have a significant effect on their affinity for the enzyme.

More precisely, the corresponding modified sequences prove to be capable of constituting potential SASPase inhibitors or activators.

By way of illustration of these potential modulators, peptide substrates having at least the following sequences may more particularly be proposed:

```
        EFDLELIEED      SEQ ID NO: 31

EFDLDLIEED      SEQ ID NO: 32

EFDLDLIEWD      SEQ ID NO: 33

EFDLDLIHWD      SEQ ID NO: 34

EPNLDLIEED      SEQ ID NO: 35
```

An activator effect of the substrates represented by the sequences SEQ ID NO: 31 and SEQ ID NO: 32 has in particular been noted.

Consequently, the present invention also relates to the use of a chemical or biological compound, for preparing a composition intended to interact with a polypeptide, the peptide sequence of which comprises at least one sequence chosen from SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 16, SEQ ID NO: 25, SEQ ID NO: 27 and SEQ ID NO: 30, and homologs thereof, and more particularly with a polypeptide of sequence SEQ ID NO: 5, SEQ ID NO: 6, SEQ ID NO: 7, SEQ ID NO: 16, SEQ ID NO: 25, SEQ ID NO: 27 or SEQ ID NO: 30, or to modulate the biological activity thereof.

This biological compound may in particular be a protease having a specific site for recognition and/or for binding and for cleavage within the amino acid sequence of said polypeptide, and preferably of a polypeptide having, as primary sequence, the sequence SEQ ID NO: 5, SEQ ID NO: 6, SEQ ID NO: 7, SEQ ID NO: 16, SEQ ID NO: 25 or SEQ ID NO: 27.

As it happens, it has been shown that inhibitors of proteases of the retropepsin type also show an effect with respect to the activity of the SASPase protein. By way of illustration of the inhibitors which may be used according to the invention, mention may in particular be made of retropepsin inhibitors, in particular sold by Bachem.

This inhibitor may also be selected so as to interfere with the dimerization of the SASPase (SEQ ID NO: 5) or of one of its activated forms represented by SEQ ID NO: 6, SEQ ID NO: 16, SEQ ID NO: 25 or SEQ ID NO: 27, prior to its proteolytic activity. This inhibitor may also be an endogenous inhibitor capable of specifically inhibiting the SASPase or its autoactivation.

Similarly, this biological compound may be an activator. By way of representation thereof, mention may in particular be made of the RP3 retropepsin modulator characterized in example VIII hereinafter.

It may also be an antibody specific for said polypeptide.

Similarly, the present invention extends to the use of a biological or chemical compound, for preparing a composition intended to inhibit the dimerization of the polypeptide of sequence SEQ ID NO: 5, SEQ ID NO: 6, SEQ ID NO: 7, SEQ ID NO: 16, SEQ ID NO: 25 or SEQ ID NO: 27.

A subject of the present invention is also the use of a polypeptide, the sequence of which comprises at least, and in particular is represented by, a sequence chosen from SEQ ID NO: 31, SEQ ID NO: 32, SEQ ID NO: 33, SEQ ID NO: 34 and SEQ ID NO: 35, for preparing a composition intended to modulate the activity of the SASPase.

The pharmaceutical or cosmetic compositions claimed and considered according to the invention may be compositions used in the cosmetics, dermatological, dermatocosmetics and pharmacological fields.

A physiologically acceptable medium is, according to the invention, a cosmetically or pharmaceutically acceptable medium that is compatible with the skin, the mucous membranes, and nails and/or the hair.

The compositions according to the invention can be applied to the nails, the hair, and more particularly to the skin and the mucous membranes.

They are particularly advantageous for acting on one or more epidermal mechanisms such as the degradation of protein(s), the activation of enzyme(s), and/or the regulation of the epidermal differentiation/proliferation phenomenon.

As it happens, the compositions according to the invention are particularly useful for compensating for an imbalance in epidermal differentiation/proliferation. More particularly, they may be useful for regulating the phenomena of moisturization, of inflammation, of melanogenesis and/or of desquamation, the aging phenomenon, the defense mechanisms, for the regulation of differentiation/proliferation on certain cell and skin types: keratinocytes, melanocytes, Langerhans cells, sebocytes, adipocytes, and also the regulation of secretion phenomena and of invasion processes.

More precisely, the claimed compositions prove to be advantageous in the following areas:
  for treating dermatological complaints associated with a keratinization disorder relating to differentiation and to proliferation, in particular for treating common acne, comedo-type acne, polymorphic acne, rosacea, nodulocystic acne, acne conglobata, senile acne, and secondary acne such as solar, drug-related or occupational acne, for treating other types of keratinization conditions, in particular ichtyoses, ichtyosiform conditions, Darrier's disease, palmoplantar kerato-derma, leukoplakia and leukoplakiform conditions, and cutaneous or mucosal (oral) lichen, for treating other dermatological complaints associated with a keratinization condition, with an inflammatory and/or immunoallergic component, and in particular all forms of psoriasis, whether cutaneous, mucosal or ungual psoriasis, and even psoriatic rheumatism, or alternatively cutaneous atopy, such as eczema, or urticaria or else gingival hypertrophy; the compounds may also be used in certain inflammatory ailments not exhibiting any keratinization condition, for treating all dermal or epidermal proliferations, whether benign or malignant, whether or not of viral origin, such as common warts, flat warts and epidermodysplasia verruciformis, oral or florid papillomatoses, and proliferations which may be induced by ultraviolet light, in particular in the case of basal-cell and spinocellular epithelioma, for treating other dermatological disorders such as bullous dermatoses and collagen diseases, for repairing or combating skin aging, whether it is photo-induced or chronological, or for reducing actinic keratoses and pigmentations, or any pathological conditions associated with chronological or actinic aging, for preventing or curing stigmata of epidermal and/or dermal atrophy induced by local or systematic corticosteroids, or any other form of skin atrophy, for preventing or treating cicatrization conditions or for preventing or repairing stretch marks, and for combating sebaceous function conditions such as hyperseborrhea of acne or simple seborrhea.

In the case of an application in the cosmetic field, in particular for body and hair hygiene, the compositions according to the invention are in particular useful for treating skin with a tendency to suffer from acne, for hair regrowth, for anti-hairloss, for combating the greasy appearance of the skin or of the hair, in protection against the harmful aspects of the sun or in the treatment of physiologically dry skin, for preventing and/or combating photoinduced or chronological aging. They may also be useful for improving reconstructed skin. The polypeptide and/or its derivatives and/or modulators of its activity or of its activation can also be used directly in the culture medium.

Another subject of the invention is a method of cosmetic treatment intended to combat skin conditions associated with a dysfunction of cell proliferation and/or differentiation, such as in particular dry skin, hyperkeratosis, parakeratosis, sebogenesis conditions, neoplasias and/or signs of skin aging, characterized in that a cosmetic composition comprising at least one polypeptide, the peptide sequence of which comprises at least one sequence chosen from SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 16, SEQ ID NO: 25 and SEQ ID NO: 27, and in particular which is represented wholly or partly by SEQ ID NO: 5, SEQ ID NO: 6, SEQ ID NO: 7, SEQ ID NO: 16, SEQ ID NO: 25 or SEQ ID NO: 27, and more particularly which has the sequence SEQ ID NO: 5, SEQ ID NO: 6, SEQ ID NO: 7, SEQ ID NO: 16, SEQ ID NO: 25 or SEQ ID NO: 27, or a mixture derived from the proteolysis of one of these polypeptides, is applied to the skin, the mucous membranes and/or the keratin fibers.

The method of treatment of the invention is a cosmetic method intended to improve the esthetic appearance of the individual experiencing epidermal proliferation and/or differentiation conditions.

The invention also relates to the use of a polypeptide, the peptide sequence of which comprises at least one sequence chosen from SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 16, SEQ ID NO: 25 and SEQ ID NO: 27, and in particular which is represented wholly or partly by SEQ ID NO: 5, SEQ ID NO: 6, SEQ ID NO: 7, SEQ ID NO: 16, SEQ ID NO: 25 or SEQ ID NO: 27, and more particularly which has the sequence SEQ ID NO: 5, SEQ ID NO: 6, SEQ ID NO: 7, SEQ ID NO: 16, SEQ ID NO: 25 or SEQ ID NO: 27, or of a mixture derived from the proteolysis of one of these polypeptides, for preparing a pharmaceutical composition intended for the treatment of dermatological ailments, and in particular those mentioned above.

In particular, the invention relates to the use of a polypeptide or of a mixture as described above, for preparing a pharmaceutical composition intended to treat ichtyosis, psoriasis or any pathology involving hyperkeratosis or parakeratosis or having an inflammatory component. They may also be pain-killing compositions, or compositions for treating certain skin diseases such as eczema, rosacea, psoriasis, lichens or severe pruritus.

Insofar as the polypeptides of sequence SEQ ID NO: 5, SEQ ID NO: 6, SEQ ID NO: 16, SEQ ID NO: 25 or SEQ ID NO: 27 have considerable structural homologies with retro-viral proteins, as is shown in the examples and in FIG. 4, an in particular with those of the human immunodeficiency virus, they are also capable of behaving like agents capable of modulating viral infection or of being modulated by certain viral antiproteases.

Consequently, a subject of the invention is also the use of a polypeptide, the peptide sequence of which comprises at least one sequence chosen from SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 16, SEQ ID NO: 25 and SEQ ID NO: 27, and homologs thereof, and in particular is represented wholly or partly by SEQ ID NO: 5, SEQ ID NO: 6, SEQ ID NO: 7, SEQ ID NO: 16, SEQ ID NO: 25 and SEQ ID NO: 27, and more particularly which has the sequence SEQ ID NO: 5, SEQ ID NO: 6, SEQ ID NO: 7, SEQ ID NO: 16, SEQ ID NO: 25 and SEQ ID NO: 27, for preparing an antiviral composition.

These compositions may in particular be useful for treating epidermal pathologies associated with a virus of the papillomavirus, Herpes or HIV type.

Similarly, such compositions may be advantageous for treating side effects related to inhibition of the endogenous SASPase by the medicinal products directed against these viruses or other pathological viruses. More particularly, this specific application of the polypeptides according to the invention takes advantage of the structural homology observed between the SASPase and viral retropepsins, as illustrated by the examples hereinafter.

The treatment generally involves application of the composition as described above to the skin of the individual to be treated.

A subject of the present invention is also the use of a polypeptide, the peptide sequence of which is chosen from the sequences SEQ ID NO: 1, SEQ ID NO: 4, SEQ ID NO: 5, SEQ ID NO: 6, SEQ ID NO: 7, SEQ ID NO: 8, SEQ ID NO 9, SEQ ID NO: 16 and SEQ ID NO: 25 or SEQ ID NO 27, as a tool in a diagnostic or screening method, or for preparing a diagnostic tool.

More precisely, the invention is directed toward the use of a polypeptide, the peptide sequence of which is chosen from SEQ ID NO: 1, SEQ ID NO: 4, SEQ ID NO: 5, SEQ ID NO: 6, SEQ ID NO: 7, SEQ ID NO: 8, SEQ ID NO 9, SEQ ID NO: 16, SEQ ID NO: 25 and SEQ ID NO: 27, and homologs thereof, more particularly of a polypeptide which has the sequence SEQ ID NO: 5, SEQ ID NO: 6, SEQ ID NO: 7, SEQ ID NO: 16, SEQ ID NO: 25 or SEQ ID NO: 27, or of its proteolytic fragments and of any synthetic peptide deduced from its sequence, for preparing or purifying, optionally from epidermis, any molecule capable of modulating its interaction with possible ligands.

In addition, the invention is directed toward the use of a polypeptide, the peptide sequence of which is chosen from SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 16, SEQ ID NO: 25 and SEQ ID NO: 27, and homologs thereof, and more particularly of a polypeptide which has the sequence SEQ ID NO: 5, SEQ ID NO: 6, SEQ ID NO: 7, SEQ ID NO: 16, SEQ ID NO: 25 or SEQ ID NO: 27, of its proteolytic fragments or of any synthetic peptide deduced from its sequence, for selecting novel antiviral molecules having fewer side effects.

A subject of the invention is also the use of a polypeptide, the peptide sequence of which is chosen from SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 16, SEQ ID NO: 25 and SEQ ID NO: 27, and homologs thereof, and more particularly of a polypeptide which has the sequence SEQ ID NO: 5, SEQ ID NO 6, SEQ ID NO: 7, SEQ ID NO: 16, SEQ ID NO: 25 or SEQ ID NO: 27, of its proteolytic fragments or of any synthetic peptide deduced from its sequence, for preparing specific antisera and/or monoclonal antibodies aimed in particular at purifying said polypeptide and its fragments, or at modulating its activity.

By extension, a subject of the invention is also any use of said sequence for producing recombinant antibodies or antibody fragments, whatever the biological system used to produce them.

A subject of the invention is also a polyclonal or monoclonal antibody characterized in that it specifically recognizes a polypeptide, the peptide sequence of which is represented wholly or partly by SEQ ID NO: 5, SEQ ID NO: 6, SEQ ID NO: 7, SEQ ID NO: 16, SEQ ID NO: 25 or SEQ ID NO: 27, and more particularly which consists of the sequence SEQ ID NO: 5, SEQ ID NO: 6, SEQ ID NO: 7, SEQ ID NO: 16, SEQ ID NO: 25 or SEQ ID NO: 27.

The invention is also directed toward the use of this antibody, for preparing a composition intended for the diagnosis of a deficiency in or of an overexpression of the SASPase protein (SEQ ID NO: 5).

It also relates to the use of an antibody, for preparing a composition aimed at blocking the activity of and/or activating the SASPase in the treatment of pathologies characterized by an overexpression and/or an exaggerated activity of the SASPase.

The antibody may be an antibody prepared by immunization of any animal species that can be used for this purpose, particularly the rabbit. The antibody may be prepared by immunization using a polypeptide of the invention, whether this polypeptide is of natural, synthetic or recombinant origin, preferably purified.

It is known that a protein is synthesized in cells based on a deoxyribonucleic acid (DNA) matrix encoding said protein. It is also known that the genetic code is degenerate. Thus, the amino acid sequence of the polypeptide of the invention may be derived from various deoxyribonucleic acid sequences, which may be natural or synthetic. The term "synthetic deoxyribonucleic acid sequence" is here intended to mean any sequence obtained chemically or by genetic manipulation.

Said deoxyribonucleic acid sequences may be derived from any possible origins, namely either animal, in particular mammalian, and even more particularly human origin, or plant origin, or from microorganisms (viruses, phages, bacteria, inter alia) or else from fungi, without prejudice regarding whether or not they are naturally present in said organism of origin.

As it happens, the invention relates to the isolated and purified deoxyribonucleic acid fragments encoding the claimed polypeptides.

In the course of these studies, the applicant has been able to isolate and purify the deoxyribonucleic acid fragments encoding the primary amino acid sequences of the polypeptides of sequence SEQ ID NO: 5, SEQ ID NO: 6, SEQ ID NO: 7, SEQ ID NO: 16, SEQ ID NO: 25 or SEQ ID NO: 27, from human skin.

A subject of the invention is an isolated and purified deoxyribonucleic acid fragment, the nucleotide sequence of which comprises at least the coding nucleotide sequence SEQ ID NO: 24, and in particular is represented by the coding nucleotide sequence SEQ ID NO: 19, SEQ ID NO: 20, SEQ ID NO: 24, SEQ ID NO: 26 or SEQ ID NO: 28.

The nucleic acid sequences according to the invention may in particular be used for preparing corresponding sense or antisense ribonucleic acid sequences.

A subject of the invention is also any poly-nucleotide, ribonucleic acid or deoxyribonucleic acid, which may be sense or antisense, in particular "small interfering RNA", corresponding at least to the coding nucleotide sequence SEQ ID NO: 19, SEQ ID NO: 20, SEQ ID NO: 24, SEQ ID NO: 26 or SEQ ID NO: 28.

The nucleic acid sequences of the invention can also be used to prepare oligonucleotide primers which hybridize, under high stringency conditions, with the sequence SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 26 and SEQ ID NO: 28.

These sense and/or antisense oligonucleotide primers may be useful for sequencing reactions or specific amplification reactions according to the "PCR" (polymerase chain reaction) technique or any other variant thereof with the aim of cloning, identifying or diagnosing a polypeptide represented by SEQ ID NO: 1, SEQ ID NO: 4, SEQ ID NO 5, SEQ ID NO: 6, SEQ ID NO: 7, SEQ ID NO: 8, SEQ ID NO: 9, SEQ ID NO: 16, SEQ ID NO: 25 or SEQ ID NO: 27.

In particular, the probes or primers of the invention are labeled prior to their use. For this, several techniques are within the scope of those skilled in the art, such as, for example, fluorescent, radioactive, chemiluminescent or enzymatic labeling.

The in vitro diagnostic methods in which these nucleotide probes are used for detecting synthesis of nucleic acid sequences encoding a polypeptide according to the invention are included in the present invention.

The DNA fragment corresponding to the sequence SEQ ID NO: 19, SEQ ID NO: 20, SEQ ID NO: 24, SEQ ID NO: 26 or SEQ ID NO: 28 can also be introduced into an expression vector, thus allowing the synthesis of a corresponding "recombinant" protein.

A subject of the invention is therefore also a recombinant expression vector containing all or part of the coding nucleotide sequence SEQ ID NO: 19, SEQ ID NO: 20, SEQ ID NO: 24, SEQ ID NO: 26 or SEQ ID NO: 28.

A subject of the invention is also a cosmetic or pharmaceutical composition comprising, in a physiologically acceptable medium, a natural or synthetic deoxyribonucleic acid sequence encoding the primary amino acid sequence of a polypeptide in accordance with the invention or a sense or antisense ribonucleic acid sequence, in particular interfering antisense ribonucleic acid, corresponding to said sequence SEQ ID NO: 19, SEQ ID NO: 20, SEQ ID NO: 24, SEQ ID NO: 26 or SEQ ID NO: 28.

In general, any composition of the invention may be ingested, injected or applied to the skin (on any cutaneous zone of the body) or to the mucous membranes (buccal, jugal, gingival, genital, conjunctival, etc.).

Preferably, a composition of the invention is applied to the skin or the mucous membranes.

According to the method of administration considered, it may be in any of the pharmaceutical forms normally used.

For topical application to the skin, the composition may have the form in particular of aqueous or oily solutions or of dispersions of the lotion or serum type, of emulsions with a liquid or semi-liquid consistency of the milk type, obtained by dispersion of a fatty phase in an aqueous phase (O/W) or vice versa (W/O), or of suspensions or emulsions with a soft consistency of the aqueous or anhydrous cream or gel type, or else of microcapsules or microparticles, or of vesicular dispersions of the ionic and/or nonionic type or of foams. These compositions are prepared according to the usual methods.

For injection, the composition may be in the form of aqueous or oily lotions or in the form of serums. For the eyes, it may be in the form of drops, and for ingestion, it may be in the form of capsules, of granules, of syrups or of tablets.

The amounts of the various constituents of the compositions according to the invention are those conventionally used in the fields under consideration.

In the cosmetics field, these compositions constitute in particular cleansing, protection, treatment or care creams for the face, for the hands, for the feet, for the large anatomical folds or for the body (for example day creams, night creams, makeup-removing creams, foundation creams, antisun creams), fluid foundations, makeup-removing milks, protective body milks or body care milks, antisun milks, skincare lotions, gels or foams, for instance cleansing lotions, antisun lotions, artificial tanning lotions, bath compositions, deodorant compositions comprising a bactericidal agent, aftershave gels or lotions, hair-removing creams, insect-repellent compositions, pain-relief compositions, or compositions for treating certain skin diseases, such as eczema, rosacea, psoriasis, lichens and severe pruritus.

The compositions according to the invention may also consist of solid preparations constituting cleansing soaps or bars.

The compositions may also be packaged in the form of an aerosol composition also comprising a pressurized propellant.

A composition according to the invention may also be a care composition for the scalp, and in particular a shampoo, a setting lotion, a treating lotion, a styling cream or gel, a dye composition (in particular for oxidation dyeing) optionally in the form of coloring shampoos, of restructuring lotions for the hair, a permanent-waving composition (in particular a composition for the first stage of a permanent-waving operation), a lotion or a gel for preventing hair loss, an antiparasitic shampoo, an antidandruff shampoo, etc.

A composition may also be for orodental use, for example a toothpaste. In this case, the composition may contain adjuvants and additives that are usual for compositions for oral use, and in particular surfactants, thickeners, wetting agents, polishing agents such as silica, various active ingredients such as fluorides, in particular sodium fluoride, and optionally sweeteners such as sodium saccharinate.

When the composition is an emulsion, the proportion of the fatty phase may range from approximately 5% to 80% by weight, and preferably from approximately 5% to 50% by weight, relative to the total weight of the composition. The oils, the waxes, the emulsifiers and the co-emulsifiers used in the composition in emulsion form are chosen from those conventionally used in the cosmetic field. The emulsifier and the co-emulsifier are present, in the composition, in a proportion ranging from 0.3% to 30% by weight, and preferably from 0.5% to 20% by weight, relative to the total weight of the composition. The emulsion may also contain lipid vesicles.

When the composition is an oily solution or gel, the fatty phase may represent more than 90% of the total weight of the composition.

In a known manner, the cosmetic composition may also contain adjuvants that are common in the cosmetics field, such as hydrophilic or lipophilic gelling agents, hydrophilic or lipophilic additives, preserving agents, antioxidants, solvents, fragrances, fillers, screening agents, odor absorbers and dyestuffs. The amounts of these various adjuvants are those conventionally used in the cosmetics field, and range, for example, from approximately 0.01% to 10% of the total weight of the composition. Depending on their nature, these adjuvants may be introduced into the fatty phase, into the aqueous phase and/or into the lipid spherules.

As oils or waxes which may be used in the invention, mention may be made of mineral oils (liquid petroleum jelly), plant oils (liquid fraction of karite butter, or sunflower oil), animal oils (perhydro-squalene), synthetic oils (Purcellin oil), silicone oils or waxes (cyclomethicone) and fluoro oils (perfluoropolyethers), beeswax, carnauba wax or paraffin wax. Fatty alcohols and fatty acids (stearic acid) may be added to these oils. As emulsifiers which may be used in the invention, mention may be made, for example, of glyceryl stearate, polysorbate 60 and the mixture of PEG-6/PEG-32/glycol stearate sold under the name Tefose® 63 by the company Gattefosse.

As solvents which may be used in the invention, mention may be made of lower alcohols, in particular ethanol and isopropanol, and propylene glycol.

As hydrophilic gelling agents which may be used in the invention, mention may be made of carboxyvinyl polymers (carbomer®), acrylic copolymers such as acrylate/alkyl acrylate copolymers, polyacrylamides, polysaccharides such as hydroxypropylcellulose, natural gums and clays, and, as lipophilic gelling agents, mention may be made of modified clays such as bentones, metal salts of fatty acids, such as aluminum stearates, and hydrophobic silica, ethylcellulose and polyethylene.

The composition may contain other hydrophilic active agents, such as proteins or protein hydrolysates, amino acids, polyols, urea, allantoin, sugars and sugar derivatives, water-soluble vitamins, plant extracts and hydroxy acids.

Lipophilic active agents which may be used include retinol (vitamin A) and derivatives thereof, tocopherol (vitamin E) and derivatives thereof, essential fatty acids, ceramides, essential oils, and salicylic acid and derivatives thereof.

According to the invention, the composition may combine at least one other active agent intended in particular for the prevention and/or treatment of skin ailments. Among these active agents, mention may be made, by way of example, of:

- agents for decreasing differentiation and/or proliferation and/or pigmentation of the skin, such as retinoic acid and isomers thereof, retinol and esters thereof, vitamin D and derivatives thereof, estrogens such as estradiol, kojic acid or hydroquinone;
- antibacterial agents, such as clindamycin phosphate or erythromycin or antibiotics of the tetracycline class;
- antiparasitic agents, in particular metroni-dazole, crotamiton or pyrethrinoids;
- antifungal agents, in particular compounds belonging to the imidazole class, such as econazole, ketoconazole or miconazole, or salts thereof, polyene compounds, such as amphotericin B, compounds of the allylamine family, such as terbinafin, or alternatively octopirox;
- antiviral agents such as acyclovir;
- steroidal anti-inflammatory agents, such as hydrocortisone, betamethasone valerate or clobetasol propionate, or nonsteroidal anti-inflammatory agents such as, for example, ibuprofen and salts thereof, diclofenac and salts thereof, acetylsalicylic acid, acetaminophen or glycyrrhizic acid;
- anesthetics, such as lidocaine hydrochloride and derivatives thereof;
- antipruriginous agents, such as thenaldine, trimeprazine or cyproheptadine;
- keratolytic agents, such as α- and β-hydroxy-carboxylic acids or β-keto carboxylic acids, their salts, amides or esters and more particularly hydroxy acids such as glycolic acid, lactic acid, salicylic acid, citric acid and fruit acids in general, and 5-n-octanoylsalicylic acid;
- free-radical scavengers, such as a-tocopherol or esters thereof, superoxide dismutases, certain metal chelating agents, or ascorbic acid and esters thereof;
- antiseborrheic agents, such as progesterone;
- antidandruff agents, such as octopirox or zinc pyrithione;
- antiacne agents, such as retinoic acid or benzoyl peroxide.

Thus, according to the particular embodiment, the composition according to the invention also comprises at least one agent chosen from antibacterial, antiparasitic, antifungal, antiviral, anti-inflammatory and antipruriginous agents, anesthetics, keratolytic agents, free-radical scavengers, antiseborrheic agents, antidandruff agents, antiacne agents and/or agents for decreasing differentiation and/or proliferation and/or pigmentation of the skin.

The examples that appear hereinafter are presented by way of nonlimiting illustration of the invention.

FIGURES

Figure 2:
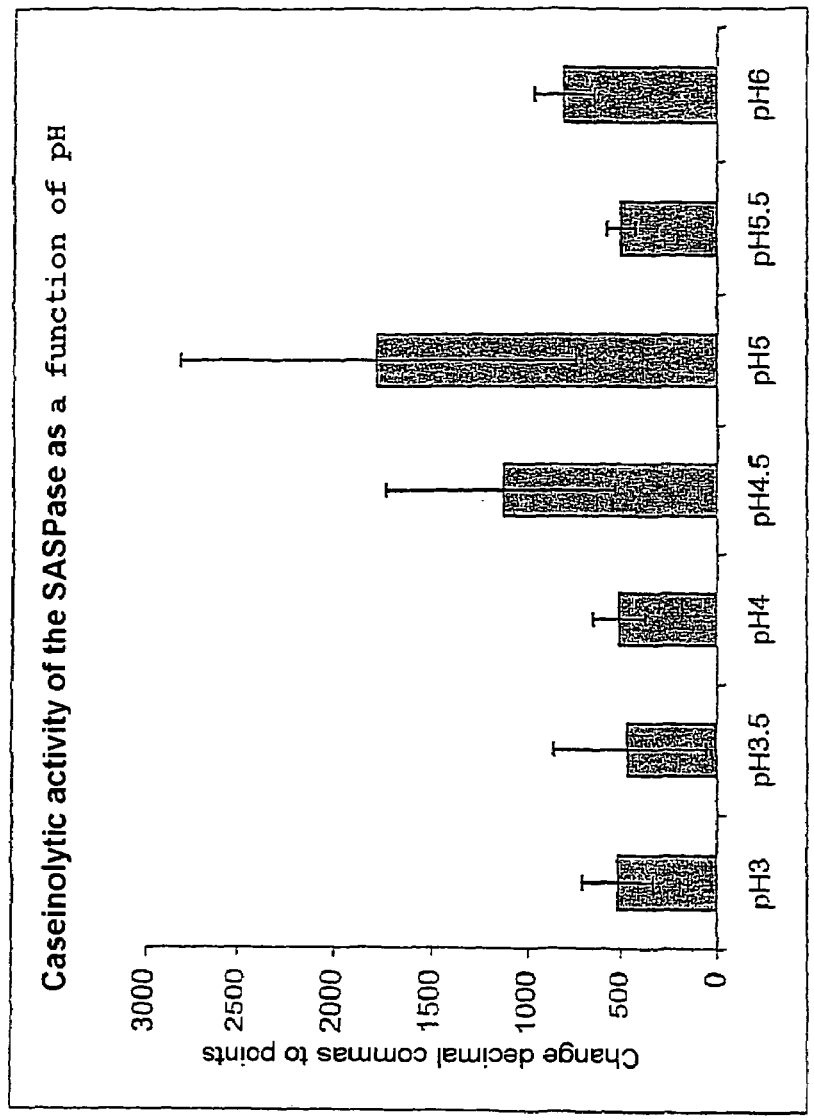
Figure 3:
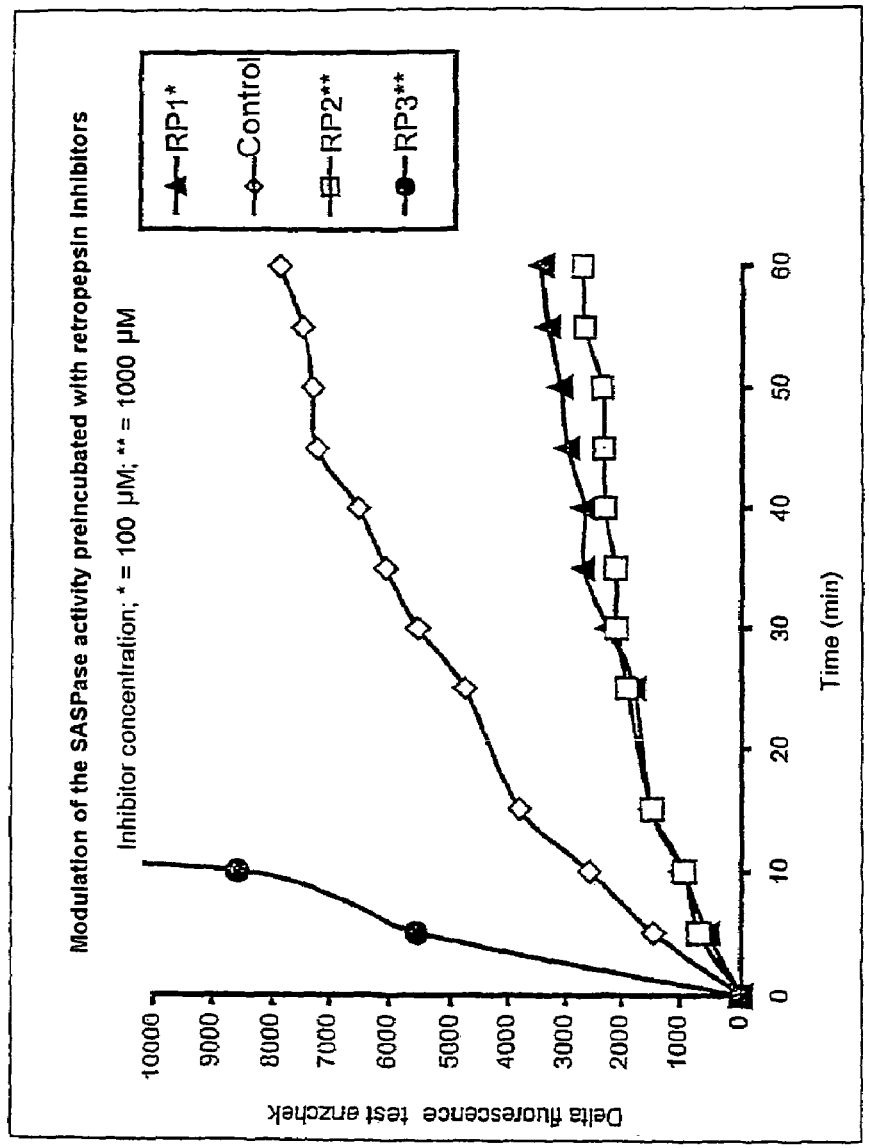
Figure 5:
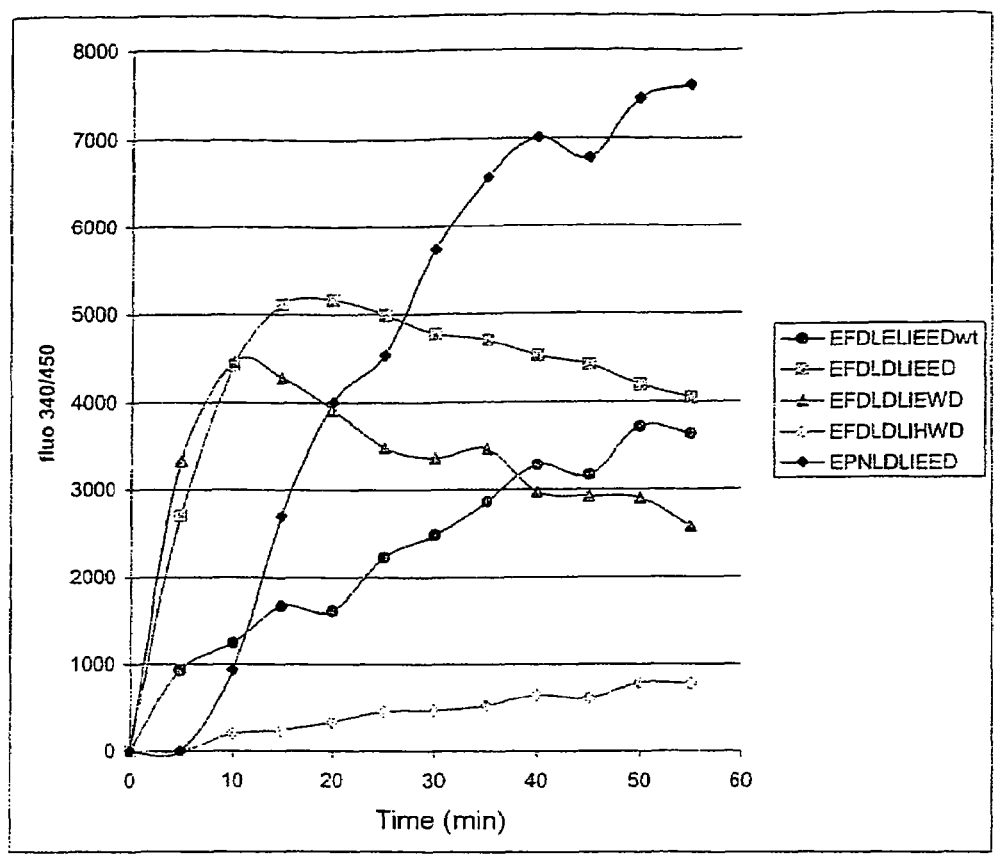

FIG. 1: photograph of the 2D electrophoresis gel obtained according to example I, FIG. 2: representation of the influence of pH on the proteolytic activity of the SASPase, FIG. 3: analysis of the activity of a certain number of conventional modulators with respect to the proteolytic activity of the SASPase, FIG. 4: representation of the structural homologies between the SASPase (SEQ ID NO: 39) and proteases FIAV (SEQ ID NO: 37) and HIV2 (SEQ ID NO: 38), FIG. 5: representation of the hydrolysis of the substrates represented by the sequences SEQ ID NO: 31, SEQ ID NO: 32, SEQ ID NO: 33, SEQ ID NO: 34 and SEQ ID NO: 35, by the SASPase.

EXAMPLES

Materials

The oligonucleotides used in the various experiments are given below in table I.

TABLE I

| Primer name | Sequence 5' to 3' | SEQ ID N° |
|---|---|---|
| SC 130 | GATAGGATCCATGGCCGGGAGCGGAGCCAGGAG | 12 |
| SC 131 | TTGAATTCTCAGTGGGATAGCTCCTGCCGC | 11 |
| SC 134 | GGCCCTGGGTGTCTACAATA | 13 |
| SC 135 | TTGGCCACCTTTACCACATT | 14 |
| SC 140 | TAGGATCCATGGGGAGCCCAGGGGC | 10 |

Not I-(dT)$_{18}$ is an oligonucleotide sold by the company Amersham Pharmacia Biotech Not I-(dT)$_{18}$ is designed so as to bind to long series of A, for example poly A+ series. Used in reverse transcription reactions, Not I-(dT)$_{18}$ binds to the poly A+.

Example I

Identification and Isolation of the SASPase by Two-Dimensional Gel Electrophoresis and Sequencing a) Preparation from Human Epidermis Buffers:

I: 0.3% SDS; 28 mM tris-HCl; 22 mM tris-base

2D: 8M urea; 2% (w/v) 3-[(3-cholamidopropyl)-dimethylammonio]-1-propane sulfonate (CHAPS); 20 mM dithiothreitol; 0.5% (v/v) buffer Imobiline pH gradient (IPG), pH=3 9-10, 18 cm, sold by the company Amersham Pharmacia Biotech.

Extracts of reconstructed human epidermis are prepared from 30 units of the D13 Episkin kit. 15 ml of buffer I are added to the 30 reconstructed epidermides and the entire mixture is homogenized with a Potter homogenizer, brought to the boil for 10 min, and then again homogenized with a Potter homogenizer. The solution is then centrifuged at 10 000 g for 10 min. The supernatant is collected and filtered through a 0.22 µm membrane. 12 ml of supernatant SI are thus obtained. Cold acetone (10 v/2 v) is then added to the supernatant SI. After incubation for 20 min, the mixture obtained is centrifuged at 9400 g for 10 min. The supernatant is then removed and the pellet is dried at ambient temperature for 20 min. The pellet is then taken up in 2 ml of 2D buffer. The extract EI is thus obtained. The final protein concentration is 11 mg/ml.

b) Two-Dimensional Gel

The two-dimensional separation of the proteins contained in the extract EI is carried out on a Pharmacia device (model Multiphor II). The two-dimensional separation of the proteins was carried out according to the supplier's recommendations, except that, for the re-equilibration of the IPG gel after migration in the first direction, the iodoacetamide was omitted. The staining of the spots, the recovery thereof and the sequencing of the polypeptides that they contained were carried out according to the techniques described in Mehul B, Bernard D, Simonetti L, Bernard M A, Schmidt R: Identification and cloning of a new calmodulin-like protein from human epidermis. J Biol Chem 275: 12841-12347, 2000, or else "A practical guide to protein and peptide purification for microsequencing" (editor Paul Matsudaira, second edition, 1993). Represented in FIG. 1 is the corresponding electrophoresis gel.

The proteins were detected by amido black staining. The spots corresponding to proteins identified by Edman sequencing are located with the name of these proteins. The spot called SASPase makes it possible to locate an epidermal form of the protein having an apparent MW of 12 kD and a pI of 5.8.

The results obtained made it possible to characterize the sequences SEQ ID NO: 1, SEQ ID NO: 2 and SEQ ID NO: 3.

Example II

Isolation of the cDNA Encoding the SASPase from Human Keratinocytes and Expression of the SASPase (SEQ ID NO: 5) and of its Truncated (Δ1-84) Form (SEQ ID NO: 4)

a) Preparation of the cDNA

The total RNA of keratinocytes originating from reconstructed human epidermis after 13 days of culture was prepared using the "RNeasy kit®" for preparing RNA, and purified using the "QIAshredder column®" kit, sold by the company Qiagen, according to the supplier's instructions.

The complementary DNAs (cDNAs) of the RNAs thus prepared were synthesized using the "First Strand cDNA Synthesis®" kit sold by the company Amersham Pharmacia Biotech, according to the supplier's instructions, using the oligonucleotide Not I-(dT)$_{18}$ as primer.

cDNA fragments encoding the complete SASPase thus obtained were amplified by polymerase chain reactions (PCRs) in a "Thermocycler®" device sold by the company Perkin-Elmer, using a DNA polymerase, pfu, sold by the company Promega and, as primers, the pair of oligonucleotides SC140 (SEQ ID NO: 10)/SC131 (SEQ ID NO: 11) and the following conditions: 1 cycle (95° C. for 2 min), 35 cycles (94° C. for 30 sec, 65° C. for 30 sec, 72° C. for 2 min) and 1 cycle (72° C. for 7 min).

Similarly, cDNA fragments encoding the truncated form of the SASPase (SEQ ID NO: 4), lacking the 84 N-terminal amino acids of the SASPase, referred to as Δ1-84, were amplified by PCR using, as primers, the pair of oligonucleotides SC131/SC130 (SEQ ID NO: 11 and SEQ ID NO: 12).

b) Construction and Expression of the Recombinant SASPase (rSASPase)

The SASPase cDNA obtained above is introduced into the plasmid vector pGex-4T-3 sold by the company Amersham Pharmacia Biotech, by cleavage/ligation at the BamH-1/EcoR1 restriction site. This recombinant plasmid which contains, in phase in the reading frame, the coding sequence of the SASPase (SEQ ID NO: 5) and the coding sequence of glutathione S-transferase (GST) is then introduced into *E. coli* strain BL21 (DE3) sold by the company Amersham Pharmacia Biotech. The recombinant fusion protein expressed by the bacteria can be cleaved with thrombin under gentle conditions, the construct being such that the fusion protein obtained carries a site for cleavage by this protease.

The expression product is purified by affinity chromatography on a gluthathione-sepharose column.

All these experiments were carried out by strictly applying the various protocols from the suppliers.

The SDS-PAGE gel electrophoresis analysis of an aliquot fraction of the expression product obtained by carrying out the method described above shows that this method makes it possible to obtain a satisfactory amount of the recombinant fusion protein GST-SASPase.

Similarly, the expression, in a satisfactory amount, of the recombinant fusion protein GST-truncated SASPase Δ1-84 (SEQ ID NO: 4) was obtained.

Example III

Obtaining the Activated SASPase (SEQ ID NO: 6)

The recombinant fusion protein GST-SASPase Δ1-84 (SEQ ID NO: 4) eluted from the glutathione-sepharose column, obtained in example II, is incubated with thrombin in PBS buffer, at pH 8, for 18 hours at 22° C. The buffer is exchanged by filtration on Biorad G25® gel against a 100 mM acetate solution, pH 4.5. The mixture thus obtained is subjected to cationic chromatography using an NaCl gradient (0 to 1 M NaCl). The fractions containing the GST and the thrombin are eliminated and the fraction eluted with the 750 mM NaCl solution is recovered. An SDS-PAGE gel electrophoresis analysis carried out on the fraction eluted with the 750 mM NaCl solution, containing caseinolytic activity (data not shown), shows the presence of a major band which, by comparison with the molecular mass markers, has an apparent molecular mass of 12 kD and a minor band which corresponds to the truncated SASPase form Δ1-84 (SEQ ID NO: 4).

The 12 kD form corresponds to the activated form of the SASPase. The Edman sequencing indicates that the isolated product corresponds to the activated SASPase (SEQ ID NO: 6).

Example IV

Obtaining the Activated SASPase (SEQ ID NO: 25)

The deletion of the site encoding the FANS sequence on the truncated form of the SASPase (SEQ ID NO: 4), using the Quick Change Site-directed Mutagenesis kit (Stratagene) and suitable primers, is carried out using as DNA matrix the plasmid construct of the SASPase C27 sequence (SEQ ID NO: 4) in the vector pGEX-4T3.

A protein, the protein sequence of which is represented by SEQ ID NO: 36, is obtained.

After incubation of this new protein at pH 5.00 in acetate buffer, there is, surprisingly, generation of a low molecular weight fragment (approximately 21 kDa by SDS-PAGE electrophoresis) which has at most the sequence SEQ ID NO: 25 of theoretical mass 18731.44.

SEQ ID NO: 27, of theoretical mass 16794.43, is obtained from SEQ ID NO: 25 by assuming a C-terminal activation identical to the form SEQ ID NO: 6.

Example V

Characterization of the Proteolytic Activity of the SASPase Protein a) Activity with Respect to a Substrate This activity was demonstrated according to the following protocol:

The oxidized beta-chain of insulin (Sigma) is used as substrate. The concentration is 50 µg in 1.5 ml of 0.1 M acetate buffer, pH 5.0. 50 µl of 12 kD SASPase (SEQ ID NO: 6) (approximately 1 mg/ml) purified by gel filtration are added so as to initialize the hydrolysis. Controls without enzyme or without substrate are used. Over time (1 h to 24 h at 37° C.), HPLCs are performed in order to follow the hydrolysis. The peaks that appear rapidly correspond to the main hydrolysis sites and those that only appear after 24 h correspond to the secondary sites. The peaks are collected after they have been fractionated, and are N-terminal sequences (EDMAN sequencing, Pasteur Institute).

```
FVNQHLCGSHLVEALYLVCGERGFF.    (SEQ ID NO: 15)
```

Main site: E/A (pepsin-like)

Secondary sites: L/Y and Y/L (pepsin-like)

These results show that the activated SASPase is capable of degrading insulin. Heat denaturation (95° C., 10 min) of the SASPase abolishes its insulin-degrading activity. Its caseinolytic activity was, moreover, demonstrated (results not shown).

b) Autocatalytic Activity

In this second assay, it is the GST-SASPase protein (SEQ ID NO: 4) which is itself used as a substrate by autocatalysis.

The GST-SASPase, at 3 mg/ml in 0.1 M phosphate buffer, pH 7.0, containing 50% glycerol, is rapidly acidified to pH 5.0 with 1 M acetate buffer, pH 4.5. At each incubation time, at 37° C., an aliquot is taken and the reaction is blocked by adding an equivalent volume of Laemmli buffer without DTT. At the end of the kinetics, each sample is analyzed by SDS-PAGE electrophoresis (15% acrylamide gel), demonstrating a gradual appearance of a major band that migrates at an apparent MW of 12 kD subsequent to the disappearance of the fusion protein.

This assay shows that it is also possible to obtain the activated SASPase (SEQ ID NO: 6) directly by acidification at pH 3 to 6, preferably 4 to 6, of the recombinant fusion protein GST-rSASPase Δ1-84 or GST-SASPase obtained in example I, followed by a gel filtration (G75) purification step.

Furthermore, analysis of the activated solutions by Edman sequencing and by QTOF mass spectrometry gives, for the autoactivated protease, three cleavage sites that are more or less equivalent in terms of probabilities:

F/A (like certain metalloproteases in the skin)

N/S (cleavage site not listed)

E/L (only described for matrilysin, which is capable of activating urokinase and MMPs 1, 2 and 9).

Example VI

Site-Directed Mutations on the Active Site of the SASPase Proving that it Belongs to the Aspartic Acid Protease Family The Quick Change Site-directed Mutagenesis kit (Stratagene) is used for producing the SASPase mutants.

The SASPase sequence SEQ ID NO: 5 is modified at aspartic acid No. 212, i.e. on its potential active site. To do this, two oligonucleotides are synthesized such that amino acid 212 is substituted either to alanine (mutant A/D), or to glutamic acid (mutant E/D).

A PCR amplification is carried out with each pair of mutated oligonucleotides, and the plasmid construct of the SASPase C27 sequence in the vector pGEX-4T3 is used as DNA matrix.

Competent bacteria (XL1 blue) are then transformed with each PCR product. Several clones are amplified and sequenced in order to verify the presence of the desired mutation and only of this mutation.

Autocleavage of the SASPase C27 and of its Mutants:

The mutated recombinant proteins are produced according to the same protocol as for the wild-type form, SASPase C27; (SEQ ID NO: 4).

Each recombinant protein produced in fusion protein form is then incubated in a 1 M acetate buffer, pH 4.5, at 37° C. Samples are taken over time and are analyzed by SDS-PAGE.

A decrease in the whole form GST-SASPase C27 is observed over time, which demonstrates an autocleavage and, consequently, an autoactivation; numerous lower molecular weight bands appear. The mutated forms (A/D) and (E/D), for their part, do not autoactivate.

This experiment confirms the involvement of aspartic acid No. 212 in the active site of the SASPase.

Example VII

Analysis of the SASPase Expression by Northern Blotting, RT-PCR in Human Tissues and in Keratinocytes The analyses were carried out by Northern blotting, using commercial polyA+RNA blot membranes (Ambion®) according to the protocol described by the manufacturer, and by RT-PCR using a cDNA collection of the human "rapid-scan®" membranes sold by the company OriGene Technologies, Inc.

The Northern blotting analysis was carried out using, as probe, the cDNA encoding the (truncated Δ1-84) form of the SASPase (SEQ ID NO: 4) isolated from the recombinant plasmid prepared in example II, and using a membrane containing various RNA samples.

The PCR is carried out using the Taq polymerase sold by the company Promega, and the pair of oligonucleotides SC134 (SEQ ID NO: 13)/SC135 (SEQ ID NO 14) as primers, under the following conditions:

1 cycle of 3 min at 94° C., 25 to 30 cycles (94° C. for 30 sec, 53° C. for 30 sec, 72° C. for 60 sec), and 1 cycle at 72° C. for 5 min.

The resulting PCR products are visualized by ethidium bromide staining after separation on a 2% (weight/volume) agarose gel.

From the results, it emerges that the SASPase is substantially expressed in virtually all the tissues tested, at a low level in fetal liver, fetal brain, ovary, adrenal gland, thyroid, placenta, testes, stomach, muscle, lung, liver, spleen and heart, and at an even lower level in bone marrow, pancreas, saliva and small intestine. This expression is, on the other hand significant in the brain and particularly very high in the skin.

Example VIII

Oligomerization of the SASPase Using a Crosslinking Reagent

The protocol used is based on the technique described in T. D. Meek et al.; Proc, Natl. Acad. Sci. USA vol. 86, pages 1841-1845, March 1989.

A study of the crosslinking using BS3 (Pierce) is carried out on activated SASPase (SEQ ID NO: 6), obtained by acidification and purification by exclusion chromatography (gel filtration) of the recombinant fusion protein GST-SASPase Δ1-84.

1 μg of BS3 in 60 μl of 50 mM phosphate buffer, pH 7, containing 150 mM NaCl, 0.1% TX100 and 5 mM EDTA is added to the activated SASPase (SEQ ID NO: 6) obtained in example III, placed in ice. A control sample free of BS3 is also prepared. After 90 min, 2 μl of 1 M Tris-HCl, pH 8, are introduced into the reaction media in order to stop the reaction. The products obtained are then analyzed by gel filtration and by SDS-PAGE electrophoresis.

The activated SASPase incubated with BS3 forms a stable multimeric complex which, by gel filtration, separates into three major peaks. Three distinct bands can also be observed on a gel after SDS-PAGE electrophoresis, the apparent molecular masses of which bands, determined by comparison with the molecular mass markers, are respectively 12 kD, and between 10-14 kD, 30-45 kD and 60-100 kD.

Example IX

Influence of pH on the Proteolytic Activity of SASPase

10 μl of GST-SASPase Δ1-84 fusion proteins (approximately 3 mg/ml) obtained in example II are incubated in 200 μl of 0.1 M acetate buffer, adjusted to various pH values in the presence of the casein substrate sold under the name Enzchek® by the company Molecular Probes, and used at the concentrations recommended by the supplier.

Each assay is repeated three times.

After incubation at 37° C. for 20 hours, the fluorescence is measured on a plate reader sold under the name Biolumin® by the company Molecular Probes, using the excitation/emission couple: 485/535 nm. The results are given in FIG. 2.

These results show that, under the experimental conditions selected, the enzymatic activity of the SASPase is pH-dependent and is optimal at pH 5. Moreover, assays that are not shown, in 0.1 M phosphate buffer of pH 6 to 7.5, show only a weak residual activity.

The influence of pH on the autoactivation is also determined and shows that the optimum pH is between 3 and 6.9, and preferably between 4 and 6.

Example X

Study of the Effect of Various Inhibitors of the Aspartic Acid Protease Family on the Caseinolytic Activity of the Activated SASPase (SEQ ID NO: 6)

10 μl of activated SASPase (SEQ ID NO: 6) that have been autoactivated (approximately 3 mg/ml) are added to 200 μl of 0.1 M acetate buffer, pH 5.5, containing 20 μl of DMSO with retropepsin inhibitors. A control assay is carried out under the same conditions in the absence of inhibitor.

The mixture is pre-incubated at 4° C. for 1 hour, and the substrate, casein, sold under the name Enzchek® by the company Molecular Probes, is then added in sufficient amount to obtain the concentration recommended by the supplier, the solutions having been heated to 37° C. beforehand.

The casein hydrolysis is followed by measuring the fluorescence on a Biolumin® plate reader sold by the company Molecular Probes, using the excitation/emission couple: 485/535 nm.

The results obtained are given in FIG. 3. It is noted that the kinetics for casein hydrolysis, in the presence of the RP1 and RP2 retropepsin inhibitors, are lower than the control. The activity of the SASPase is therefore inhibited by these inhibitors.

RP1 corresponds to the sequence Ac-Leu-Val-Phe-aldehyde and is sold by Bachem under the reference N 1395.0005, RP2 corresponds to the sequence Ac-Leu-Leu-Met-aldehyde and is sold by Bachem under the reference N 1315.0005 and RP3 corresponds to the sequence Ac-Leu-Leu-Nle-aldehyde and is sold by Bachem under the reference N 1320.0005.

It is also noted that the kinetics for casein hydrolysis, in the presence of the RP3 retropepsin inhibitor, are significantly higher than those obtained under the control conditions. The activity of the SASPase therefore appears to be stimulated by this inhibitor.

Example XI

Study of the Effect of the Activated SASPase (SEQ ID NO: 6) on the Degradation of Corneodesmosin Extracted from Human Stratum Corneum a) Principle Corneodesmosin is a marker for desquamation since it is involved in corneocyte cohesion at corneodesmosomes. The more the protein is degraded, the more significant is the detachment of the corneocytes. Corneodesmosin degradation is therefore a key step of desquamation.

The test used in this study therefore consists in following this degradation in the presence of the test substance.

b) Preparation of the Sample

Acetone powders are prepared using stripping varnish (Mehul B, Bernard D, Simonetti L, Bernard MA, Schmidt R: Identification and cloning of a new calmodulin-like protein from human epidermis. J Biol Chem 275: 12841-12347, 2000), taken from the lower parts of the legs of volunteers with dry skin. Aliquot fractions of 2 mg of stratum corneum powder are introduced separately into Eppendorf tubes, and then immersed in the test solutions in a proportion of 100 μl/mg. The solutions are prepared in acetate buffer, pH 5. A control without protease is prepared in parallel in order to evaluate the natural degradation of corneodesmosin. For each test, three samples are prepared. The samples, trials and control, are incubated at 30° C., with stirring for 24 hours.

c) Extraction, Separation and Detection of Proteins

The proteins are extracted with complete Laemmli buffer. They are assayed by the Bradford method (Bio-Rad® kit). The concentration of each sample is adjusted so as to allow comparison of the samples. The polypeptides are separated by SDS-PAGE electrophoresis on a 15% acrylamide gel, and then transferred onto a PVDF membrane. Immunodetection with a solution of anti-corneodesmosin antibody used at $\frac{1}{12500}$ and of secondary antibody coupled to peroxidase makes it possible to visualize the corneodesmosin. The bands detected by chemiluminescence are quantified using the Quantity One® program from the company Biorad. The membranes are then stained with amido-black, and then scanned. In addition, the keratins, which are major proteins of corneocyte extracts, are quantified in order to verify the adjustment to 0.6 mg/ml of all the samples.

A positive control for degradation (+) is prepared using 5 mM of EDTA. A trial is carried out in the presence of 60 μg of activated SASPase. A negative control represents the natural degradation of corneodesmosin under the operating conditions of the test.

d) Results

TABLE II

|  | Standardized corneodesmosin | | % Residual corneodesmosin |
|---|---|---|---|
|  | T0 | T24 h | T24 h/T0*100 |
| Activated SASPase | 33107 | 24918 | 75 |
| +control | 31657 | 26685 | 84 |
| −control | 32701 | 30546 | 93 |

A significant decrease in the percentage of residual corneodesmosin is observed when the stratum corneum acetone powders are brought into contact with the activated SASPase (SEQ ID NO: 6), compared with the controls.

Example XII

Investigation of Substrate for Demonstrating the SASPase Activity

The peptide substrate considered (SEQ ID NO 31, SEQ ID NO: 32, SEQ ID NO: 33, SEQ ID NO: 34 or SEQ ID NO: 35) quenched using the Abz/(NO₂)Tyr fluorescent system is used at 100 µM in DMSO, and then 10 µl of this stock substrate solution are added per 100 µl of 0.1 M acetate buffer, pH 5.00.

10 µg of GST-C27 (fusion protein at 1 mg/ml in PBS) are added. Incubation is carried out at 37° C. The fluorescence is read at 340/450 nm on a Biolumin plate reader at various times. The results are given in FIG. 5.

It is noted that the natural (wt) peptide is effectively hydrolyzed by the SASPase, but amino acid substitutions in the sequence of this peptide can generate substrates for which the SASPase has greater affinity.

A search (MEROPS base) of the various proteases capable of cleaving peptide bonds that are hydrolyzed or hydrolyzable by the SASPase (combinations of the various amino acids found in position P1 with the amino acids found in position P2 of the sequences hydrolyzed by the SASPase) reveals, in parallel with retroviral-type proteases, proteases which have been described as being important for skin: SCCE (desquamation, conversion of proIL1B), MMP1, MMP2 and MMP9 (cicatrization, etc.), mu Calpain (maturation of the cornified envelope, filaggrin processing), thrombin (activation of protease activated receptors), convertases 1, 2, 4, 5 and 7 (filaggrin processing, regulation of differentiation, etc.).

These observations support the idea that the SASPase has an important role in skin physiology.

The invention claimed is:

1. A cosmetic or pharmaceutical composition comprising, in a physiologically acceptable medium, at least one purified, natural or synthetic polypeptide, wherein said polypeptide consists of at least one amino acid sequence selected from the group consisting of SEQ ID NO: 4, SEQ ID NO: 5, and SEQ ID NO: 6.

2. The composition as claimed in claim 1, wherein said polypeptide consists of SEQ ID NO: 5 or SEQ ID NO: 6.

3. The composition as claimed in claim 1, wherein said polypeptide is further prepared as a dimeric or other multimeric form.

4. The composition as claimed in claim 1, wherein said polypeptide has further undergone one or more post-translational modifications.

5. The composition as claimed in claim 2, wherein said polypeptide is further fused with another polypeptide, a hydrophilic or hydrophobic targeting agent or a bioconversion precursor.

6. The composition as claimed in claim 1, wherein said polypeptide consists of SEQ ID NO: 6.

7. An isolated and purified polypeptide belonging to the aspartic acid protease family and consisting of SEQ ID NO: 6.

8. The polypeptide as claimed in claim 7, having an apparent molecular mass of between 5 and 30 kD.

9. The polypeptide as claimed in claim 8, having an apparent molecular mass of between 9 and 15 kD.

10. The polypeptide as claimed in claim 9, having an apparent molecular mass of between 11 and 14 kD.

11. The polypeptide as claimed in claim 7, wherein said polypeptide is further prepared as a dimeric or other multimeric form.

12. The polypeptide as claimed in claim 7, having a theoretical isoelectric point of between 3 and 9.

13. The polypeptide as claimed in claim 7, said polypeptide being of natural origin and purified from mammalian tissues.

14. The polypeptide as claimed in claim 13, wherein said polypeptide is purified from human epidermis or other human skin.

15. The polypeptide as claimed in claim 7, wherein said polypeptide has further undergone one or more post-translational modifications.

16. The polypeptide as claimed in claim 7 wherein said polypeptide is further fused with another polypeptide, a hydrophilic or hydrophobic targeting agent or a bioconversion precursor.

17. A method for degrading corneodesmosin in corneocytes comprising applying to corneocytes an effective corneodesmosin degrading amount of at least one polypeptide, wherein said polypeptide comprises at least one amino acid sequence selected from the group consisting of SEQ ID NO: 4, SEQ ID NO: 5 and SEQ ID NO: 6.

* * * * *

SEQUENCE LISTING

```
<160> NUMBER OF SEQ ID NOS: 39

<210> SEQ ID NO 1
<211> LENGTH: 12
<212> TYPE: PRT
<213> ORGANISM: Homo Sapiens

<400> SEQUENCE: 1

Phe Leu Val Asp Ser Gly Ala Gln Val Ser Val Val
1               5                   10

<210> SEQ ID NO 2
<211> LENGTH: 21
<212> TYPE: PRT
<213> ORGANISM: Homo Sapiens

<400> SEQUENCE: 2

Ala Gln Phe Leu Val Ala Asn Ala Ser Ala Glu Glu Ala Ile Ile Gly
1               5                   10                  15

Thr Asp Val Leu Gln
            20

<210> SEQ ID NO 3
<211> LENGTH: 9
<212> TYPE: PRT
<213> ORGANISM: Homo Sapiens

<400> SEQUENCE: 3

Ile Leu Gly Val Trp Asp Thr Ala Val
1               5

<210> SEQ ID NO 4
<211> LENGTH: 259
<212> TYPE: PRT
<213> ORGANISM: Homo Sapiens

<400> SEQUENCE: 4
```

```
Met Ala Gly Ser Gly Ala Arg Ser Glu Glu Gly Arg Arg Gln His Ala
1               5                   10                  15

Phe Val Pro Glu Pro Phe Asp Gly Ala Asn Val Val Pro Asn Leu Trp
            20                  25                  30

Leu His Ser Phe Glu Val Ile Asn Asp Leu Asn His Trp Asp His Ile
            35                  40                  45

Thr Lys Leu Arg Phe Leu Lys Glu Ser Leu Arg Gly Glu Ala Leu Gly
50                  55                  60

Val Tyr Asn Arg Leu Ser Pro Gln Asp Gln Gly Asp Tyr Gly Thr Val
65                  70                  75                  80

Lys Glu Ala Leu Leu Lys Ala Phe Gly Val Pro Gly Ala Ala Pro Ser
                85                  90                  95

His Leu Pro Lys Glu Ile Val Phe Ala Asn Ser Met Gly Lys Gly Tyr
            100                 105                 110

Tyr Leu Lys Gly Lys Ile Gly Lys Val Pro Val Arg Phe Leu Val Asp
            115                 120                 125

Ser Gly Ala Gln Val Ser Val Val His Pro Asn Leu Trp Glu Glu Val
            130                 135                 140

Thr Asp Gly Asp Leu Asp Thr Leu Gln Pro Phe Glu Asn Val Val Lys
145                 150                 155                 160

Val Ala Asn Gly Ala Glu Met Lys Ile Leu Gly Val Trp Asp Thr Ala
                165                 170                 175

Val Ser Leu Gly Lys Leu Lys Leu Lys Ala Gln Phe Leu Val Ala Asn
            180                 185                 190

Ala Ser Ala Glu Glu Ala Ile Ile Gly Thr Asp Val Leu Gln Asp His
            195                 200                 205

Asn Ala Ile Leu Asp Phe Glu His Arg Thr Cys Thr Leu Lys Gly Lys
            210                 215                 220

Lys Phe Arg Leu Leu Pro Val Gly Gly Ser Leu Glu Asp Glu Phe Asp
225                 230                 235                 240

Leu Glu Leu Ile Glu Glu Asp Pro Ser Ser Glu Glu Gly Arg Gln Glu
                245                 250                 255

Leu Ser His

<210> SEQ ID NO 5
<211> LENGTH: 343
<212> TYPE: PRT
<213> ORGANISM: Homo Sapiens

<400> SEQUENCE: 5

Met Gly Ser Pro Gly Ala Ser Leu Gly Ile Lys Lys Ala Leu Gln Ser
1               5                   10                  15

Glu Gln Ala Thr Ala Leu Pro Ala Ser Ala Pro Ala Val Ser Gln Pro
            20                  25                  30

Thr Ala Pro Ala Pro Ser Cys Leu Pro Lys Ala Gly Gln Val Ile Pro
            35                  40                  45

Thr Leu Leu Arg Glu Ala Pro Phe Ser Ser Val Ile Ala Pro Thr Leu
50                  55                  60

Leu Cys Gly Phe Leu Phe Leu Ala Trp Val Ala Ala Glu Val Pro Glu
65                  70                  75                  80

Glu Ser Ser Arg Met Ala Gly Ser Gly Ala Arg Ser Glu Glu Gly Arg
                85                  90                  95

Arg Gln His Ala Phe Val Pro Glu Pro Phe Asp Gly Ala Asn Val Val
            100                 105                 110
```

```
Pro Asn Leu Trp Leu His Ser Phe Glu Val Ile Asn Asp Leu Asn His
        115                 120                 125

Trp Asp His Ile Thr Lys Leu Arg Phe Leu Lys Glu Ser Leu Arg Gly
    130                 135                 140

Glu Ala Leu Gly Val Tyr Asn Arg Leu Ser Pro Gln Asp Gln Gly Asp
145                 150                 155                 160

Tyr Gly Thr Val Lys Glu Ala Leu Leu Lys Ala Phe Gly Val Pro Gly
                165                 170                 175

Ala Ala Pro Ser His Leu Pro Lys Glu Ile Val Phe Ala Asn Ser Met
                180                 185                 190

Gly Lys Gly Tyr Tyr Leu Lys Gly Lys Ile Gly Lys Val Pro Val Arg
            195                 200                 205

Phe Leu Val Asp Ser Gly Ala Gln Val Ser Val Val His Pro Asn Leu
        210                 215                 220

Trp Glu Glu Val Thr Asp Gly Asp Leu Asp Thr Leu Gln Pro Phe Glu
225                 230                 235                 240

Asn Val Val Lys Val Ala Asn Gly Ala Glu Met Lys Ile Leu Gly Val
                245                 250                 255

Trp Asp Thr Ala Val Ser Leu Gly Lys Leu Lys Leu Lys Ala Gln Phe
                260                 265                 270

Leu Val Ala Asn Ala Ser Ala Glu Glu Ala Ile Ile Gly Thr Asp Val
            275                 280                 285

Leu Gln Asp His Asn Ala Ile Leu Asp Phe Glu His Arg Thr Cys Thr
        290                 295                 300

Leu Lys Gly Lys Lys Phe Arg Leu Leu Pro Val Gly Gly Ser Leu Glu
305                 310                 315                 320

Asp Glu Phe Asp Leu Glu Leu Ile Glu Glu Asp Pro Ser Ser Glu Glu
                325                 330                 335

Gly Arg Gln Glu Leu Ser His
            340

<210> SEQ ID NO 6
<211> LENGTH: 138
<212> TYPE: PRT
<213> ORGANISM: Homo Sapiens

<400> SEQUENCE: 6

Ala Asn Ser Met Gly Lys Gly Tyr Tyr Leu Lys Gly Lys Ile Gly Lys
1               5                   10                  15

Val Pro Val Arg Phe Leu Val Asp Ser Gly Ala Gln Val Ser Val Val
            20                  25                  30

His Pro Asn Leu Trp Glu Glu Val Thr Asp Gly Asp Leu Asp Thr Leu
        35                  40                  45

Gln Pro Phe Glu Asn Val Lys Val Ala Asn Gly Ala Glu Met Lys
    50                  55                  60

Ile Leu Gly Val Trp Asp Thr Ala Val Ser Leu Gly Lys Leu Lys Leu
65                  70                  75                  80

Lys Ala Gln Phe Leu Val Ala Asn Ala Ser Ala Glu Glu Ala Ile Ile
                85                  90                  95

Gly Thr Asp Val Leu Gln Asp His Asn Ala Ile Leu Asp Phe Glu His
            100                 105                 110

Arg Thr Cys Thr Leu Lys Gly Lys Lys Phe Arg Leu Leu Pro Val Gly
        115                 120                 125

Gly Ser Leu Glu Asp Glu Phe Asp Leu Glu
```

```
            130             135

<210> SEQ ID NO 7
<211> LENGTH: 58
<212> TYPE: PRT
<213> ORGANISM: Homo Sapiens

<400> SEQUENCE: 7

Met Gly Ser Pro Gly Ala Ser Leu Gly Ile Lys Lys Ala Leu Gln Ser
1               5                   10                  15

Glu Gln Ala Thr Ala Leu Pro Ala Ser Ala Pro Ala Val Ser Gln Pro
            20                  25                  30

Thr Ala Pro Ala Pro Ser Cys Leu Pro Lys Ala Gly Gln Val Ile Pro
        35                  40                  45

Thr Leu Leu Arg Glu Ala Pro Phe Ser Ser
    50                  55

<210> SEQ ID NO 8
<211> LENGTH: 18
<212> TYPE: PRT
<213> ORGANISM: Homo Sapiens

<400> SEQUENCE: 8

Val Ile Ala Pro Thr Leu Leu Cys Gly Phe Leu Phe Leu Ala Trp Val
1               5                   10                  15

Ala Ala

<210> SEQ ID NO 9
<211> LENGTH: 17
<212> TYPE: PRT
<213> ORGANISM: Homo Sapiens

<400> SEQUENCE: 9

Leu Ile Glu Glu Asp Pro Ser Ser Glu Glu Gly Arg Gln Glu Leu Ser
1               5                   10                  15

His

<210> SEQ ID NO 10
<211> LENGTH: 25
<212> TYPE: DNA
<213> ORGANISM: Artificial Sequence
<220> FEATURE:
<223> OTHER INFORMATION: Primer SC140 amplified by PCR encoding the
      complete SASPase.

<400> SEQUENCE: 10
taggatccat ggggagccca ggggc                                           25

<210> SEQ ID NO 11
<211> LENGTH: 30
<212> TYPE: DNA
<213> ORGANISM: Artificial Sequence
<220> FEATURE:
<223> OTHER INFORMATION: Primer SC131 amplified by PCR encoding the
      complete SASPase.

<400> SEQUENCE: 11
ttgaattctc agtgggatag ctcctgccgc                                      30

<210> SEQ ID NO 12
<211> LENGTH: 33
<212> TYPE: DNA
<213> ORGANISM: Artificial Sequence
```

-continued

```
<220> FEATURE:
<223> OTHER INFORMATION: Primer SC130 amplified by PCR encoding the
      truncated form of SASPase, Delta 1-84.

<400> SEQUENCE: 12
gataggatcc atggccggga gcggagccag gag                                    33

<210> SEQ ID NO 13
<211> LENGTH: 20
<212> TYPE: DNA
<213> ORGANISM: Artificial Sequence
<220> FEATURE:
<223> OTHER INFORMATION: Primer SC134 amplified by RT-PCR.

<400> SEQUENCE: 13
ggccctgggt gtctacaata                                                   20

<210> SEQ ID NO 14
<211> LENGTH: 20
<212> TYPE: DNA
<213> ORGANISM: Artificial Sequence
<220> FEATURE:
<223> OTHER INFORMATION: Primer SC135 amplified by RT-PCR.

<400> SEQUENCE: 14
ttggccacct ttaccacatt                                                   20

<210> SEQ ID NO 15
<211> LENGTH: 25
<212> TYPE: PRT
<213> ORGANISM: Homo Sapiens

<400> SEQUENCE: 15

Phe Val Asn Gln His Leu Cys Gly Ser His Leu Val Glu Ala Leu Tyr
1               5                   10                  15

Leu Val Cys Gly Glu Arg Gly Phe Phe
            20                  25

<210> SEQ ID NO 16
<211> LENGTH: 136
<212> TYPE: PRT
<213> ORGANISM: Homo Sapiens

<400> SEQUENCE: 16

Ser Met Gly Lys Gly Tyr Tyr Leu Lys Gly Ile Gly Lys Val Pro
1               5                   10                  15

Val Arg Phe Leu Val Asp Ser Gly Ala Gln Val Ser Val Val His Pro
            20                  25                  30

Asn Leu Trp Glu Glu Val Thr Asp Gly Leu Asp Thr Leu Gln Pro
        35                  40                  45

Phe Glu Asn Val Val Lys Val Ala Asn Gly Ala Glu Met Lys Ile Leu
    50                  55                  60

Gly Val Trp Asp Thr Ala Val Ser Leu Gly Lys Leu Lys Leu Lys Ala
65                  70                  75                  80

Gln Phe Leu Val Ala Asn Ala Ser Ala Glu Glu Ala Ile Ile Gly Thr
                85                  90                  95

Asp Val Leu Gln Asp His Asn Ala Ile Leu Asp Phe Glu His Arg Thr
            100                 105                 110

Cys Thr Leu Lys Gly Lys Lys Phe Arg Leu Leu Pro Val Gly Gly Ser
        115                 120                 125

Leu Glu Asp Glu Phe Asp Leu Glu
```

<210> SEQ ID NO 17
<211> LENGTH: 36
<212> TYPE: DNA
<213> ORGANISM: Homo Sapiens
<220> FEATURE:
<221> NAME/KEY: CDS
<222> LOCATION: (1)..(36)
<223> OTHER INFORMATION:

<400> SEQUENCE: 17

| | | | | | | | | | | | |
|---|---|---|---|---|---|---|---|---|---|---|---|
| ttc | ctg | gtg | gac | tct | ggg | gcc | cag | gtc | tct | gtg gtc | 36 |
| Phe | Leu | Val | Asp | Ser | Gly | Ala | Gln | Val | Ser | Val Val | |
| 1 | | | | 5 | | | | | 10 | | |

<210> SEQ ID NO 18
<211> LENGTH: 777
<212> TYPE: DNA
<213> ORGANISM: Homo Sapiens
<220> FEATURE:
<221> NAME/KEY: CDS
<222> LOCATION: (1)..(777)
<223> OTHER INFORMATION:

<400> SEQUENCE: 18

| | | | | | | | | | | | | |
|---|---|---|---|---|---|---|---|---|---|---|---|---|
| atg | gcc | ggg | agc | gga | gcc | agg | agt | gag | gaa | ggc | cgc | cgg cag cat gcc | 48 |
| Met | Ala | Gly | Ser | Gly | Ala | Arg | Ser | Glu | Glu | Gly | Arg | Arg Gln His Ala |
| 1 | | | | 5 | | | | | 10 | | | 15 |

| ttc | gtc | ccg | gaa | cct | ttt | gat | ggg | gcc | aat | gtc | gtc | cca aac ctc tgg | 96 |
| Phe | Val | Pro | Glu | Pro | Phe | Asp | Gly | Ala | Asn | Val | Val | Pro Asn Leu Trp |
| | | 20 | | | | | 25 | | | | | 30 |

| ctg | cac | agc | ttt | gaa | gtc | atc | aat | gac | ctc | aac | cat | tgg gac cat atc | 144 |
| Leu | His | Ser | Phe | Glu | Val | Ile | Asn | Asp | Leu | Asn | His | Trp Asp His Ile |
| 35 | | | | | 40 | | | | | 45 | | |

| acc | aag | cta | agg | ttc | ctg | aaa | gag | tcc | ctc | aga | gga | gag gcc ctg ggt | 192 |
| Thr | Lys | Leu | Arg | Phe | Leu | Lys | Glu | Ser | Leu | Arg | Gly | Glu Ala Leu Gly |
| 50 | | | | | 55 | | | | | 60 | | |

| gtc | tac | aat | agg | ctc | agt | ccc | cag | gac | cag | gga | gac | tat ggg act gtg | 240 |
| Val | Tyr | Asn | Arg | Leu | Ser | Pro | Gln | Asp | Gln | Gly | Asp | Tyr Gly Thr Val |
| 65 | | | | 70 | | | | | 75 | | | 80 |

| aaa | gag | gcc | ctc | ctg | aag | gcc | ttt | ggg | gtc | cct | ggg | gct gcc ccc agc | 288 |
| Lys | Glu | Ala | Leu | Leu | Lys | Ala | Phe | Gly | Val | Pro | Gly | Ala Ala Pro Ser |
| | | | | 85 | | | | | 90 | | | 95 |

| cac | ctg | ccc | aaa | gag | atc | gtc | ttt | gcc | aac | agc | atg | ggt aag ggc tac | 336 |
| His | Leu | Pro | Lys | Glu | Ile | Val | Phe | Ala | Asn | Ser | Met | Gly Lys Gly Tyr |
| | | | 100 | | | | | 105 | | | | 110 |

| tat | ctc | aag | ggg | aag | att | ggc | aaa | gtg | ccc | gtg | agg | ttc ctg gtg gac | 384 |
| Tyr | Leu | Lys | Gly | Lys | Ile | Gly | Lys | Val | Pro | Val | Arg | Phe Leu Val Asp |
| | | 115 | | | | | 120 | | | | | 125 |

| tct | ggg | gcc | cag | gtc | tct | gtg | gtc | cac | cca | aac | ttg | tgg gag gag gtc | 432 |
| Ser | Gly | Ala | Gln | Val | Ser | Val | Val | His | Pro | Asn | Leu | Trp Glu Glu Val |
| | 130 | | | | | 135 | | | | | 140 | |

| act | gat | ggc | gat | ctg | gac | acc | ctg | cag | ccc | ttt | gag | aat gtg gta aag | 480 |
| Thr | Asp | Gly | Asp | Leu | Asp | Thr | Leu | Gln | Pro | Phe | Glu | Asn Val Val Lys |
| 145 | | | | | 150 | | | | | 155 | | | 160 |

| gtg | gcc | aat | ggt | gct | gaa | atg | aag | atc | ctg | ggt | gtc | tgg gat aca gcg | 528 |
| Val | Ala | Asn | Gly | Ala | Glu | Met | Lys | Ile | Leu | Gly | Val | Trp Asp Thr Ala |
| | | | | 165 | | | | | 170 | | | | 175 |

| gtg | tcc | cta | ggc | aag | ctg | aag | ctg | aag | gca | cag | ttc | cta gtg gcc aat | 576 |
| Val | Ser | Leu | Gly | Lys | Leu | Lys | Leu | Lys | Ala | Gln | Phe | Leu Val Ala Asn |
| | | | 180 | | | | | 185 | | | | 190 |

| gcg | agt | gcc | gag | gaa | gcc | atc | att | ggc | act | gat | gtg | ctc cag gac cac | 624 |

```
                Ala Ser Ala Glu Glu Ala Ile Ile Gly Thr Asp Val Leu Gln Asp His
                        195                 200                 205 aat gct atc ctg gac ttt gag cac cgc aca tgc acc ctg aaa ggg aag             672
Asn Ala Ile Leu Asp Phe Glu His Arg Thr Cys Thr Leu Lys Gly Lys
    210                 215                 220 aag ttt cgc ctt ctg cct gtg gga ggg tcc ctg gaa gat gag ttt gac             720
Lys Phe Arg Leu Leu Pro Val Gly Gly Ser Leu Glu Asp Glu Phe Asp
225                 230                 235                 240 ctg gag ctc ata gag gag gac ccc tcc tca gaa gaa ggg cgg cag gag             768
Leu Glu Leu Ile Glu Glu Asp Pro Ser Ser Glu Glu Gly Arg Gln Glu
                245                 250                 255 cta tcc cac                                                                  777
Leu Ser His <210> SEQ ID NO 19
<211> LENGTH: 1029
<212> TYPE: DNA
<213> ORGANISM: Homo Sapiens
<220> FEATURE:
<221> NAME/KEY: CDS
<222> LOCATION: (1)..(1029)
<223> OTHER INFORMATION:

<400> SEQUENCE: 19 atg ggg agc cca ggg gcc agc cta ggc atc aaa aag gct ctg cag agt              48
Met Gly Ser Pro Gly Ala Ser Leu Gly Ile Lys Lys Ala Leu Gln Ser
1               5                   10                  15 gaa cag gcc aca gca ctg cct gcc tct gcc cca gca gtc agc cag ccg              96
Glu Gln Ala Thr Ala Leu Pro Ala Ser Ala Pro Ala Val Ser Gln Pro
                20                  25                  30 acc gcg cct gct ccc tcc tgc ttg ccc aag gcc gga caa gtc atc ccc             144
Thr Ala Pro Ala Pro Ser Cys Leu Pro Lys Ala Gly Gln Val Ile Pro
            35                  40                  45 act ctg ctt cga gag gcc ccg ttt tcc agc gtg att gcg ccg aca ctg             192
Thr Leu Leu Arg Glu Ala Pro Phe Ser Ser Val Ile Ala Pro Thr Leu
        50                  55                  60 ctc tgt ggg ttt ctc ttc ttg gcg tgg gtt gct gct gag gtt cca gag             240
Leu Cys Gly Phe Leu Phe Leu Ala Trp Val Ala Ala Glu Val Pro Glu
65                  70                  75                  80 gag agc agc agg atg gcc ggg agc gga gcc agg agt gag gaa ggc cgc             288
Glu Ser Ser Arg Met Ala Gly Ser Gly Ala Arg Ser Glu Glu Gly Arg
                85                  90                  95 cgg cag cat gcc ttc gtc ccg gaa cct ttt gat ggg gcc aat gtc gtc             336
Arg Gln His Ala Phe Val Pro Glu Pro Phe Asp Gly Ala Asn Val Val
            100                 105                 110 cca aac ctc tgg ctg cac agc ttt gaa gtc atc aat gac ctc aac cat             384
Pro Asn Leu Trp Leu His Ser Phe Glu Val Ile Asn Asp Leu Asn His
        115                 120                 125 tgg gac cat atc acc aag cta agg ttc ctg aaa gag tcc ctc aga gga             432
Trp Asp His Ile Thr Lys Leu Arg Phe Leu Lys Glu Ser Leu Arg Gly
    130                 135                 140 gag gcc ctg ggt gtc tac aat agg ctc agt ccc cag gac cag gga gac             480
Glu Ala Leu Gly Val Tyr Asn Arg Leu Ser Pro Gln Asp Gln Gly Asp
145                 150                 155                 160 tat ggg act gtg aaa gag gcc ctc ctg aag gcc ttt ggg gtc cct ggg             528
Tyr Gly Thr Val Lys Glu Ala Leu Leu Lys Ala Phe Gly Val Pro Gly
                165                 170                 175 gct gcc ccc agc cac ctg ccc aaa gag atc gtc ttt gcc aac agc atg             576
Ala Ala Pro Ser His Leu Pro Lys Glu Ile Val Phe Ala Asn Ser Met
            180                 185                 190 ggt aag ggc tac tat ctc aag ggg aag att ggc aaa gtg ccc gtg agg             624
```

```
Gly Lys Gly Tyr Tyr Leu Lys Gly Lys Ile Gly Lys Val Pro Val Arg
        195                 200                 205 ttc ctg gtg gac tct ggg gcc cag gtc tct gtg gtc cac cca aac ttg      672
Phe Leu Val Asp Ser Gly Ala Gln Val Ser Val Val His Pro Asn Leu
    210                 215                 220 tgg gag gag gtc act gat ggc gat ctg gac acc ctg cag ccc ttt gag      720
Trp Glu Glu Val Thr Asp Gly Asp Leu Asp Thr Leu Gln Pro Phe Glu
225                 230                 235                 240 aat gtg gta aag gtg gcc aat ggt gct gaa atg aag atc ctg ggt gtc      768
Asn Val Val Lys Val Ala Asn Gly Ala Glu Met Lys Ile Leu Gly Val
                245                 250                 255 tgg gat aca gcg gtg tcc cta ggc aag ctg aag ctg aag gca cag ttc      816
Trp Asp Thr Ala Val Ser Leu Gly Lys Leu Lys Leu Lys Ala Gln Phe
            260                 265                 270 cta gtg gcc aat gcg agt gcc gag gaa gcc atc att ggc act gat gtg      864
Leu Val Ala Asn Ala Ser Ala Glu Glu Ala Ile Ile Gly Thr Asp Val
        275                 280                 285 ctc cag gac cac aat gct atc ctg gac ttt gag cac cgc aca tgc acc      912
Leu Gln Asp His Asn Ala Ile Leu Asp Phe Glu His Arg Thr Cys Thr
    290                 295                 300 ctg aaa ggg aag aag ttt cgc ctt ctg cct gtg gga ggg tcc ctg gaa      960
Leu Lys Gly Lys Lys Phe Arg Leu Leu Pro Val Gly Gly Ser Leu Glu
305                 310                 315                 320 gat gag ttt gac ctg gag ctc ata gag gag gac ccc tca tca gaa gaa     1008
Asp Glu Phe Asp Leu Glu Leu Ile Glu Glu Asp Pro Ser Ser Glu Glu
                325                 330                 335 ggg cgg cag gag cta tcc cac                                         1029
Gly Arg Gln Glu Leu Ser His
                340

<210> SEQ ID NO 20
<211> LENGTH: 414
<212> TYPE: DNA
<213> ORGANISM: Homo Sapiens
<220> FEATURE:
<221> NAME/KEY: CDS
<222> LOCATION: (1)..(414)
<223> OTHER INFORMATION:

<400> SEQUENCE: 20 gcc aac agc atg ggt aag ggc tac tat ctc aag ggg aag att ggc aaa       48
Ala Asn Ser Met Gly Lys Gly Tyr Tyr Leu Lys Gly Lys Ile Gly Lys
1               5                   10                  15 gtg ccc gtg agg ttc ctg gtg gac tct ggg gcc cag gtc tct gtg gtc       96
Val Pro Val Arg Phe Leu Val Asp Ser Gly Ala Gln Val Ser Val Val
                20                  25                  30 cac cca aac ttg tgg gag gag gtc act gat ggc gat ctg gac acc ctg      144
His Pro Asn Leu Trp Glu Glu Val Thr Asp Gly Asp Leu Asp Thr Leu
            35                  40                  45 cag ccc ttt gag aat gtg gta aag gtg gcc aat ggt gct gaa atg aag      192
Gln Pro Phe Glu Asn Val Val Lys Val Ala Asn Gly Ala Glu Met Lys
        50                  55                  60 atc ctg ggt gtc tgg gat aca gcg gtg tcc cta ggc aag ctg aag ctg      240
Ile Leu Gly Val Trp Asp Thr Ala Val Ser Leu Gly Lys Leu Lys Leu
65                  70                  75                  80 aag gca cag ttc cta gtg gcc aat gcg agt gcc gag gaa gcc atc att      288
Lys Ala Gln Phe Leu Val Ala Asn Ala Ser Ala Glu Glu Ala Ile Ile
                85                  90                  95 ggc act gat gtg ctc cag gac cac aat gct atc ctg gac ttt gag cac      336
Gly Thr Asp Val Leu Gln Asp His Asn Ala Ile Leu Asp Phe Glu His
            100                 105                 110
```

```
cgc aca tgc acc ctg aaa ggg aag aag ttt cgc ctt ctg cct gtg gga      384
Arg Thr Cys Thr Leu Lys Gly Lys Lys Phe Arg Leu Leu Pro Val Gly
        115                 120                 125 ggg tcc ctg gaa gat gag ttt gac ctg gag                              414
Gly Ser Leu Glu Asp Glu Phe Asp Leu Glu
    130                 135
```

<210> SEQ ID NO 21
<211> LENGTH: 174
<212> TYPE: DNA
<213> ORGANISM: Homo Sapiens
<220> FEATURE:
<221> NAME/KEY: CDS
<222> LOCATION: (1)..(174)
<223> OTHER INFORMATION:

<400> SEQUENCE: 21

```
atg ggg agc cca ggg gcc agc cta ggc atc aaa aag gct ctg cag agt      48
Met Gly Ser Pro Gly Ala Ser Leu Gly Ile Lys Lys Ala Leu Gln Ser
1               5                   10                  15 gaa cag gcc aca gca ctg cct gcc tct gcc cca gca gtc agc cag ccg      96
Glu Gln Ala Thr Ala Leu Pro Ala Ser Ala Pro Ala Val Ser Gln Pro
            20                  25                  30 acc gcg cct gct ccc tcc tgc ttg ccc aag gcc gga caa gtc atc ccc      144
Thr Ala Pro Ala Pro Ser Cys Leu Pro Lys Ala Gly Gln Val Ile Pro
        35                  40                  45 act ctg ctt cga gag gcc ccg ttt tcc agc                              174
Thr Leu Leu Arg Glu Ala Pro Phe Ser Ser
    50                  55
```

<210> SEQ ID NO 22
<211> LENGTH: 54
<212> TYPE: DNA
<213> ORGANISM: Homo Sapiens
<220> FEATURE:
<221> NAME/KEY: CDS
<222> LOCATION: (1)..(54)
<223> OTHER INFORMATION:

<400> SEQUENCE: 22

```
gtg att gcg ccg aca ctg ctc tgt ggg ttt ctc ttc ttg gcg tgg gtt      48
Val Ile Ala Pro Thr Leu Leu Cys Gly Phe Leu Phe Leu Ala Trp Val
1               5                   10                  15 gct gct                                                              54
Ala Ala
```

<210> SEQ ID NO 23
<211> LENGTH: 51
<212> TYPE: DNA
<213> ORGANISM: Homo Sapiens
<220> FEATURE:
<221> NAME/KEY: CDS
<222> LOCATION: (1)..(51)
<223> OTHER INFORMATION:

<400> SEQUENCE: 23

```
ctc ata gag gag gac ccc tcc tca gaa gaa ggg cgg cag gag cta tcc      48
Leu Ile Glu Glu Asp Pro Ser Ser Glu Glu Gly Arg Gln Glu Leu Ser
1               5                   10                  15 cac                                                                  51
His
```

<210> SEQ ID NO 24
<211> LENGTH: 408
<212> TYPE: DNA
<213> ORGANISM: Homo Sapiens

```
<220> FEATURE:
<221> NAME/KEY: CDS
<222> LOCATION: (1)..(408)
<223> OTHER INFORMATION:

<400> SEQUENCE: 24 agc atg ggt aag ggc tac tat ctc aag ggg aag att ggc aaa gtg ccc      48
Ser Met Gly Lys Gly Tyr Tyr Leu Lys Gly Lys Ile Gly Lys Val Pro
1               5                   10                  15 gtg agg ttc ctg gtg gac tct ggg gcc cag gtc tct gtg gtc cac cca      96
Val Arg Phe Leu Val Asp Ser Gly Ala Gln Val Ser Val Val His Pro
            20                  25                  30 aac ttg tgg gag gag gtc act gat ggc gat ctg gac acc ctg cag ccc     144
Asn Leu Trp Glu Glu Val Thr Asp Gly Asp Leu Asp Thr Leu Gln Pro
        35                  40                  45 ttt gag aat gtg gta aag gtg gcc aat ggt gct gaa atg aag atc ctg     192
Phe Glu Asn Val Val Lys Val Ala Asn Gly Ala Glu Met Lys Ile Leu
    50                  55                  60 ggt gtc tgg gat aca gcg gtg tcc cta ggc aag ctg aag ctg aag gca     240
Gly Val Trp Asp Thr Ala Val Ser Leu Gly Lys Leu Lys Leu Lys Ala
65                  70                  75                  80 cag ttc cta gtg gcc aat gcg agt gcc gag gaa gcc atc att ggc act     288
Gln Phe Leu Val Ala Asn Ala Ser Ala Glu Glu Ala Ile Ile Gly Thr
                85                  90                  95 gat gtg ctc cag gac cac aat gct atc ctg gac ttt gag cac cgc aca     336
Asp Val Leu Gln Asp His Asn Ala Ile Leu Asp Phe Glu His Arg Thr
            100                 105                 110 tcg acc ctg aaa ggg aag aag ttt cgc ctt ctg cct gtg gga ggg tcc     384
Ser Thr Leu Lys Gly Lys Lys Phe Arg Leu Leu Pro Val Gly Gly Ser
        115                 120                 125 ctg gaa gat gag ttt gac ctg gag                                     408
Leu Glu Asp Glu Phe Asp Leu Glu
    130                 135

<210> SEQ ID NO 25
<211> LENGTH: 172
<212> TYPE: PRT
<213> ORGANISM: Homo sapiens

<400> SEQUENCE: 25

Leu Leu Lys Ala Phe Gly Val Pro Gly Ala Ala Pro Ser His Leu Pro
1               5                   10                  15

Lys Glu Ile Val Met Gly Lys Gly Tyr Tyr Leu Lys Gly Lys Ile Gly
            20                  25                  30

Lys Val Pro Val Arg Phe Leu Val Asp Ser Gly Ala Gln Val Ser Val
        35                  40                  45

Val His Pro Asn Leu Trp Glu Glu Val Thr Asp Gly Asp Leu Asp Thr
    50                  55                  60

Leu Gln Pro Phe Glu Asn Val Val Lys Val Ala Asn Gly Ala Glu Met
65                  70                  75                  80

Lys Ile Leu Gly Val Trp Asp Thr Ala Val Ser Leu Gly Lys Leu Lys
                85                  90                  95

Leu Lys Ala Gln Phe Leu Val Ala Asn Ala Ser Ala Glu Glu Ala Ile
            100                 105                 110

Ile Gly Thr Asp Val Leu Gln Asp His Asn Ala Ile Leu Asp Phe Glu
        115                 120                 125

His Arg Thr Cys Thr Leu Lys Gly Lys Lys Phe Arg Leu Leu Pro Val
    130                 135                 140

Gly Gly Ser Leu Glu Asp Glu Phe Asp Leu Glu Leu Ile Glu Glu Asp
```

```
                145                 150                 155                 160
        Pro Ser Ser Glu Glu Gly Arg Gln Glu Leu Ser His
                        165                 170

<210> SEQ ID NO 26
<211> LENGTH: 516
<212> TYPE: DNA
<213> ORGANISM: Homo sapiens
<220> FEATURE:
<221> NAME/KEY: CDS
<222> LOCATION: (1)..(516)
<223> OTHER INFORMATION:

<400> SEQUENCE: 26 ctc ctg aag gcc ttt ggg gtc cct ggg gct gcc ccc agc cac ctg ccc        48
Leu Leu Lys Ala Phe Gly Val Pro Gly Ala Ala Pro Ser His Leu Pro
1               5                   10                  15 aaa gag atc gtc atg ggt aag ggc tac tat ctc aag ggg aag att ggc        96
Lys Glu Ile Val Met Gly Lys Gly Tyr Tyr Leu Lys Gly Lys Ile Gly
            20                  25                  30 aaa gtg ccc gtg agg ttc ctg gtg gac tct ggg gcc cag gtc tct gtg       144
Lys Val Pro Val Arg Phe Leu Val Asp Ser Gly Ala Gln Val Ser Val
        35                  40                  45 gtc cac cca aac ttg tgg gag gag gtc act gat ggc gat ctg gac acc       192
Val His Pro Asn Leu Trp Glu Glu Val Thr Asp Gly Asp Leu Asp Thr
    50                  55                  60 ctg cag ccc ttt gag aat gtg gta aag gtg gcc aat ggt gct gaa atg       240
Leu Gln Pro Phe Glu Asn Val Val Lys Val Ala Asn Gly Ala Glu Met
65                  70                  75                  80 aag atc ctg ggt gtc tgg gat aca gcg gtg tcc cta ggc aag ctg aag       288
Lys Ile Leu Gly Val Trp Asp Thr Ala Val Ser Leu Gly Lys Leu Lys
                85                  90                  95 ctg aag gca cag ttc cta gtg gcc aat gcg agt gcc gag gaa gcc atc       336
Leu Lys Ala Gln Phe Leu Val Ala Asn Ala Ser Ala Glu Glu Ala Ile
            100                 105                 110 att ggc act gat gtg ctc cag gac cac aat gct atc ctg gac ttt gag       384
Ile Gly Thr Asp Val Leu Gln Asp His Asn Ala Ile Leu Asp Phe Glu
        115                 120                 125 cac cgc aca tgc acc ctg aaa ggg aag aag ttt cgc ctt ctg cct gtg       432
His Arg Thr Cys Thr Leu Lys Gly Lys Lys Phe Arg Leu Leu Pro Val
    130                 135                 140 gga ggg tcc ctg gaa gat gag ttt gac ctg gag ctc ata gag gag gac       480
Gly Gly Ser Leu Glu Asp Glu Phe Asp Leu Glu Leu Ile Glu Glu Asp
145                 150                 155                 160 ccc tcc tca gaa gaa ggg cgg cag gag cta tcc cac                       516
Pro Ser Ser Glu Glu Gly Arg Gln Glu Leu Ser His
                165                 170

<210> SEQ ID NO 27
<211> LENGTH: 155
<212> TYPE: PRT
<213> ORGANISM: Homo sapiens

<400> SEQUENCE: 27

Leu Leu Lys Ala Phe Gly Val Pro Gly Ala Ala Pro Ser His Leu Pro
1               5                   10                  15

Lys Glu Ile Val Met Gly Lys Gly Tyr Tyr Leu Lys Gly Lys Ile Gly
            20                  25                  30

Lys Val Pro Val Arg Phe Leu Val Asp Ser Gly Ala Gln Val Ser Val
        35                  40                  45

Val His Pro Asn Leu Trp Glu Glu Val Thr Asp Gly Asp Leu Asp Thr
```

-continued

```
                        50                  55                  60
Leu Gln Pro Phe Glu Asn Val Val Lys Val Ala Asn Gly Ala Glu Met
 65                  70                  75                  80

Lys Ile Leu Gly Val Trp Asp Thr Ala Val Ser Leu Gly Lys Leu Lys
                 85                  90                  95

Leu Lys Ala Gln Phe Leu Val Ala Asn Ala Ser Ala Glu Glu Ala Ile
            100                 105                 110

Ile Gly Thr Asp Val Leu Gln Asp His Asn Ala Ile Leu Asp Phe Glu
        115                 120                 125

His Arg Thr Cys Thr Leu Lys Gly Lys Lys Phe Arg Leu Leu Pro Val
    130                 135                 140

Gly Gly Ser Leu Glu Asp Glu Phe Asp Leu Glu
145                 150                 155

<210> SEQ ID NO 28
<211> LENGTH: 465
<212> TYPE: DNA
<213> ORGANISM: Homo sapiens
<220> FEATURE:
<221> NAME/KEY: CDS
<222> LOCATION: (1)..(465)
<223> OTHER INFORMATION:

<400> SEQUENCE: 28 ctc ctg aag gcc ttt ggg gtc cct ggg gct gcc ccc agc cac ctg ccc       48
Leu Leu Lys Ala Phe Gly Val Pro Gly Ala Ala Pro Ser His Leu Pro
 1               5                  10                  15 aaa gag atc gtc atg ggt aag ggc tac tat ctc aag ggg aag att ggc       96
Lys Glu Ile Val Met Gly Lys Gly Tyr Tyr Leu Lys Gly Lys Ile Gly
            20                  25                  30 aaa gtg ccc gtg agg ttc ctg gtg gac tct ggg gcc cag gtc tct gtg      144
Lys Val Pro Val Arg Phe Leu Val Asp Ser Gly Ala Gln Val Ser Val
        35                  40                  45 gtc cac cca aac ttg tgg gag gag gtc act gat ggc gat ctg gac acc      192
Val His Pro Asn Leu Trp Glu Glu Val Thr Asp Gly Asp Leu Asp Thr
    50                  55                  60 ctg cag ccc ttt gag aat gtg gta aag gtg gcc aat ggt gct gaa atg      240
Leu Gln Pro Phe Glu Asn Val Val Lys Val Ala Asn Gly Ala Glu Met
 65                  70                  75                  80 aag atc ctg ggt gtc tgg gat aca gcg gtg tcc cta ggc aag ctg aag      288
Lys Ile Leu Gly Val Trp Asp Thr Ala Val Ser Leu Gly Lys Leu Lys
                 85                  90                  95 ctg aag gca cag ttc cta gtg gcc aat gcg agt gcc gag gaa gcc atc      336
Leu Lys Ala Gln Phe Leu Val Ala Asn Ala Ser Ala Glu Glu Ala Ile
            100                 105                 110 att ggc act gat gtg ctc cag gac cac aat gct atc ctg gac ttt gag      384
Ile Gly Thr Asp Val Leu Gln Asp His Asn Ala Ile Leu Asp Phe Glu
        115                 120                 125 cac cgc aca tgc acc ctg aaa ggg aag aag ttt cgc ctt ctg cct gtg      432
His Arg Thr Cys Thr Leu Lys Gly Lys Lys Phe Arg Leu Leu Pro Val
    130                 135                 140 gga ggg tcc ctg gaa gat gag ttt gac ctg gag                          465
Gly Gly Ser Leu Glu Asp Glu Phe Asp Leu Glu
145                 150                 155

<210> SEQ ID NO 29
<211> LENGTH: 4
<212> TYPE: PRT
<213> ORGANISM: Homo sapiens

<400> SEQUENCE: 29
```

```
Phe Ala Asn Ser
  1

<210> SEQ ID NO 30
<211> LENGTH: 6
<212> TYPE: PRT
<213> ORGANISM: Homo sapiens

<400> SEQUENCE: 30

Asp Leu Glu Leu Ile Glu
  1               5

<210> SEQ ID NO 31
<211> LENGTH: 10
<212> TYPE: PRT
<213> ORGANISM: Homo sapiens

<400> SEQUENCE: 31

Glu Phe Asp Leu Glu Leu Ile Glu Glu Asp
  1               5                  10

<210> SEQ ID NO 32
<211> LENGTH: 10
<212> TYPE: PRT
<213> ORGANISM: Homo sapiens

<400> SEQUENCE: 32

Glu Phe Asp Leu Asp Leu Ile Glu Glu Asp
  1               5                  10

<210> SEQ ID NO 33
<211> LENGTH: 10
<212> TYPE: PRT
<213> ORGANISM: Homo sapiens

<400> SEQUENCE: 33

Glu Phe Asp Leu Asp Leu Ile Glu Trp Asp
  1               5                  10

<210> SEQ ID NO 34
<211> LENGTH: 10
<212> TYPE: PRT
<213> ORGANISM: Homo sapiens

<400> SEQUENCE: 34

Glu Phe Asp Leu Asp Leu Ile His Trp Asp
  1               5                  10

<210> SEQ ID NO 35
<211> LENGTH: 10
<212> TYPE: PRT
<213> ORGANISM: Homo sapiens

<400> SEQUENCE: 35

Glu Pro Asn Leu Asp Leu Ile Glu Glu Asp
  1               5                  10

<210> SEQ ID NO 36
<211> LENGTH: 255
<212> TYPE: PRT
<213> ORGANISM: Homo sapiens

<400> SEQUENCE: 36

Met Ala Gly Ser Gly Ala Arg Ser Glu Glu Gly Arg Arg Gln His Ala
```

```
1               5                   10                  15

Phe Val Pro Glu Pro Phe Asp Gly Ala Asn Val Pro Asn Leu Trp
                20                  25                  30

Leu His Ser Phe Glu Val Ile Asn Asp Leu Asn His Trp Asp His Ile
            35                  40                  45

Thr Lys Leu Arg Phe Leu Lys Glu Ser Leu Arg Gly Glu Ala Leu Gly
        50                  55                  60

Val Tyr Asn Arg Leu Ser Pro Gln Asp Gln Gly Asp Tyr Gly Thr Val
65                  70                  75                  80

Lys Glu Ala Leu Leu Lys Ala Phe Gly Val Pro Gly Ala Ala Pro Ser
                85                  90                  95

His Leu Pro Lys Glu Ile Val Met Gly Lys Gly Tyr Tyr Leu Lys Gly
            100                 105                 110

Lys Ile Gly Lys Val Pro Val Arg Phe Leu Val Asp Ser Gly Ala Gln
        115                 120                 125

Val Ser Val Val His Pro Asn Leu Trp Glu Val Thr Asp Gly Asp
            130                 135                 140

Leu Asp Thr Leu Gln Pro Phe Glu Asn Val Val Lys Val Ala Asn Gly
145                 150                 155                 160

Ala Glu Met Lys Ile Leu Gly Val Trp Asp Thr Ala Val Ser Leu Gly
                165                 170                 175

Lys Leu Lys Leu Lys Ala Gln Phe Leu Val Ala Asn Ala Ser Ala Glu
            180                 185                 190

Glu Ala Ile Ile Gly Thr Asp Val Leu Gln Asp His Asn Ala Ile Leu
        195                 200                 205

Asp Phe Glu His Arg Thr Cys Thr Leu Lys Gly Lys Lys Phe Arg Leu
        210                 215                 220

Leu Pro Val Gly Gly Ser Leu Glu Asp Glu Phe Asp Leu Glu Leu Ile
225                 230                 235                 240

Glu Glu Asp Pro Ser Ser Glu Glu Gly Arg Gln Glu Leu Ser His
                245                 250                 255

<210> SEQ ID NO 37
<211> LENGTH: 123
<212> TYPE: PRT
<213> ORGANISM: Homo Sapiens

<400> SEQUENCE: 37

Ile Gly Phe Val Asn Tyr Asn Lys Val Gly Thr Thr Thr Thr Leu Glu
1               5                   10                  15

Lys Arg Pro Glu Ile Leu Ile Phe Val Asn Gly Tyr Pro Ile Lys Phe
                20                  25                  30

Leu Leu Asp Thr Gly Ala Asp Ile Thr Ile Leu Asn Arg Arg Asp Phe
            35                  40                  45

Gln Val Lys Asn Ser Ile Glu Asn Gly Arg Gln Asn Met Ile Gly Val
        50                  55                  60

Gly Gly Gly Lys Arg Gly Thr Asn Tyr Ile Asn Val His Leu Glu Ile
65                  70                  75                  80

Arg Asp Glu Asn Tyr Lys Thr Gln Cys Ile Phe Gly Asn Val Cys Val
                85                  90                  95

Leu Glu Asp Asn Ser Leu Ile Gln Pro Leu Leu Gly Arg Asp Asn Met
            100                 105                 110

Ile Lys Phe Asn Ile Arg Leu Val Met Ala Gln
        115                 120
```

```
<210> SEQ ID NO 38
<211> LENGTH: 99
<212> TYPE: PRT
<213> ORGANISM: Homo Sapiens

<400> SEQUENCE: 38

Pro Gln Phe Ser Leu Trp Lys Arg Pro Val Val Thr Ala Tyr Ile Glu
1               5                   10                  15

Gly Gln Pro Val Glu Val Leu Leu Asp Thr Gly Ala Asp Asp Ser Ile
            20                  25                  30

Val Ala Gly Ile Glu Leu Gly Asn Asn Tyr Ser Pro Lys Ile Val Gly
        35                  40                  45

Gly Ile Gly Gly Phe Ile Asn Thr Lys Glu Tyr Lys Asn Val Glu Ile
    50                  55                  60

Glu Val Leu Asn Lys Lys Val Arg Ala Thr Ile Met Thr Gly Asp Thr
65                  70                  75                  80

Pro Ile Asn Ile Phe Gly Arg Asn Ile Leu Thr Ala Leu Gly Met Ser
                85                  90                  95

Leu Asn Leu

<210> SEQ ID NO 39
<211> LENGTH: 138
<212> TYPE: PRT
<213> ORGANISM: Homo Sapiens

<400> SEQUENCE: 39

Ala Asn Ser Met Gly Lys Gly Tyr Tyr Leu Lys Gly Lys Ile Gly Lys
1               5                   10                  15

Val Pro Val Arg Phe Leu Val Asp Ser Gly Ala Gln Val Ser Val Val
            20                  25                  30

His Pro Asn Leu Trp Glu Glu Val Thr Asp Gly Asp Leu Asp Thr Leu
        35                  40                  45

Gln Pro Phe Glu Asn Val Val Lys Val Ala Asn Gly Ala Glu Met Lys
    50                  55                  60

Ile Leu Gly Val Trp Asp Thr Ala Val Ser Leu Gly Lys Leu Lys Leu
65                  70                  75                  80

Lys Ala Gln Phe Leu Val Ala Asn Ala Ser Ala Glu Glu Ala Ile Ile
                85                  90                  95

Gly Thr Asp Val Leu Gln Asp His Asn Ala Ile Leu Asp Phe Glu His
            100                 105                 110

Arg Thr Cys Thr Leu Lys Gly Lys Lys Phe Arg Leu Leu Pro Val Gly
            115                 120                 125

Gly Ser Leu Glu Asp Glu Phe Asp Leu Glu
        130                 135
```